(12) United States Patent
Liu et al.

(10) Patent No.: US 8,361,932 B2
(45) Date of Patent: Jan. 29, 2013

(54) DETECTION OF PROTEASE AND PROTEASE ACTIVITY USING A SINGLE NANOSCRESCENT SERS PROBE

(75) Inventors: Gang L. Liu, Berkeley, CA (US); Jonathan A. Ellman, Oakland, CA (US); Luke P. Lee, Orinda, CA (US); Fanqing Frank Chen, Moraga, CA (US)

(73) Assignee: The Regents of the University of California, Oakland, CA (US)

( * ) Notice: Subject to any disclaimer, the term of this patent is extended or adjusted under 35 U.S.C. 154(b) by 686 days.

(21) Appl. No.: 12/299,284

(22) PCT Filed: May 2, 2007

(86) PCT No.: PCT/US2007/010722
§ 371 (c)(1),
(2), (4) Date: Sep. 14, 2009

(87) PCT Pub. No.: WO2008/018933
PCT Pub. Date: Feb. 14, 2008

(65) Prior Publication Data
US 2010/0048412 A1    Feb. 25, 2010

Related U.S. Application Data

(60) Provisional application No. 60/797,525, filed on May 3, 2006.

(51) Int. Cl.
*C40B 30/04* (2006.01)
*C40B 40/10* (2006.01)
*G01N 33/573* (2006.01)

(52) U.S. Cl. ................. 506/9; 435/7.4; 506/18

(58) Field of Classification Search .......... None
See application file for complete search history.

(56) References Cited

U.S. PATENT DOCUMENTS

| | | | |
|---|---|---|---|
| 5,306,403 A * | 4/1994 | Vo-Dinh | 204/450 |
| 2005/0048639 A1 | 3/2005 | Wallach et al. | |
| 2005/0272114 A1 | 12/2005 | Darzins et al. | |
| 2006/0008924 A1 | 1/2006 | Anker et al. | |
| 2006/0024808 A1 | 2/2006 | Darzins et al. | |

FOREIGN PATENT DOCUMENTS

WO    WO 2008/018933    2/2008

OTHER PUBLICATIONS

Lu et al. Nanophotonic Crecent Moon Structures with Sharp Edge for Ultrasensitive Biomolecular Detection by Local Electromagnetic Field Enhancement Effect. Nanoletters. Published in the Web: Dec. 8, 2004. Year 2005, vol. 5, Nol. 1, pp. 119-124.*
International Search Report and Written Opinion dated Jul. 31, 2008 issued in WO/2008/018933 (PCT/U52007/010722).
International Preliminary Report on Patentability dated Nov. 4, 2008 issued in WO/2008/018933 (PCT/U52007/010722).
Chinese Ofiice Action dated Oct. 27, 2011 issued in 200780024900.8 (English Translation).
European Extended Search report dated May 13, 2009 issued in EP07835744.9.
European Intent to Grant dated Mar. 16, 2010 issued in EP07835744. 9.
Acevedo et al. (2002) "Development and validation of a quantitative ELISA for the measurement of PSA concentration." *Clin. Chim. Acta* 317: 55-63.
Bjartell et al. (1999) "Time-resolved fluorescence imaging (TRFI) for direct immunofluorescence of PSA and alpha-1-antichymotrypsin in prostatic tissue sections." *Prostate Cancer P D* 2(3): 140-147.
Brillard-Bourdet et al. (2002) "Amidolytic activity of prostatic acid phosphatase on human semenogelins and semenogelin-derived synthetic substrates." *Eur. J. Biochem.* 269: 390-395.
Charrier et al. (1999) "Two-dimensional electrophoresis of prostate-specific antigen in sera of men with prostate cancer or benign prostate hyperplasia." *Electrophoresis* 20(4-5): 1075-1081.
Crawford (2003) "Epidemiology of prostate cancer." *Urology* 62(Suppl 6A): 3-12.
Denmeade et al. (1997) "Specific and efficient peptide substrates for assaying the proteolytic activity of prostate-specific antigen." *Cancer Res* 57:4924-4930.
Denmeade et al. (2002) "A History of prostate cancer treatment." *Nat. Rev. Cancer* 2: 389-396.
Denmeade et al. (2003) "Prostate-Specific Antigen-Activated Thapsigargin Prodrug as Targeted Therapy for Prostate Cancer" *J. Natl. Cancer Inst.* 95(13): 990-1000.
Denmeade et al. (2004) "The role of prostate-specific antigen in the clinical evaluation of prostatic disease" *BJU Int* 93 Suppl 1: 10-15.
Gronberg et al. (2003) "Prostate cancer epidemiology" *Lancet* 361: 859-864.
Haes et al. (2005) "Detection of a biomarker for alzheimer's disease from synthetic and clinical samples using a nanoscale optical biosensor" *J. Am. Chem. Soc.* 127(7): 2264-2271.
Jackson et al. (2004) "Surface-enhanced Raman scattering on tunable plasmonic nanoparticle substrates" *Proc. Natl. Acad. Sci. USA*, 101(52): 17930-17935.
Liu et al. (2005) "Magnetic Nanocrescents as Controllable Surface Enhanced Raman Scattering Nanoprobes for Biomolecular Imaging." *Adv. Mater.* 17: 2683-88.
Liu et al. (2005) "Nanowell surface enhanced Raman scattering arrays fabricated by soft lithography for label-free biomolecular detections in integrated microfluidics." *Appl. Phys. Letts.* 87: 074101-3.
Liu et al. (2006) "Optofluidic control using photothermal nanoparticles" *Nat Mater* 5: 27-32.
Liu et al. (2006) "Peptide-Nanoparticle Hybrid SERS Probe for Dynamic Detection of Active Cancer Biomarker Enzymes" *Conf Proc IEEE Eng Med Biol Soc.* 1:795-798.

(Continued)

*Primary Examiner* — Marcela M Cordero Garcia
(74) *Attorney, Agent, or Firm* — Tom Hunter; Weaver Austin Villeneuve & Sampson LLP

(57) ABSTRACT

This invention pertains to the in vitro detection of proteases using a single peptide-conjugate nanocrescent surface enhanced Raman scattering (SERS) probes with at least nanomolar sensitivity. The probe enables detection of proteolytic activity in extremely small volume and at low concentration. In certain embodiments the probes comprise an indicator for the detection of an active protease, where the indicator comprises a nanocrescent attached to a peptide, where said peptide comprises a recognition site for the protease and a Raman tag attached to the peptide.

31 Claims, 10 Drawing Sheets

OTHER PUBLICATIONS

Lu et al. (2005) "High-density silver nanoparticle film with temperature-controllable interparticle spacing for a tunable surface enhanced Raman scattering substrate." *Nano Lett.* 5(1): 5-9.

Lu et al. (2005) "Nanophotonic crescent moon structures with sharp edge for ultrasenstive biomolecular detection by local electromagnetic field enhancement effect" *Nano Lett.* 5(1): 119-124.

Malm et al. (2000) "Enzymatic action of prostate-specific antigen (PSA or hK3): substrate specificity and regulation by Zn(2+), a tight-binding inhibitor." *Prostate* 45: 132(2)-139.

Mikolajczyk et al. (2003) "Pro PSA: a more cancer specific form of prostate specific antigen for the early detection of prostate cancer." *Keio J. Med.* 52(2): 86-91.

Mikolajczyk et al. (2004) "Are multiple markers the future of prostate cancer diagnostics?" *Clin. Biochem.* 37(7): 519-528.

Mikolajczyk et al. (2004) "Proenzyme Forms of Prostate-Specific Antigen in Serum Improve the Detection of Prostate Cancer" *Clin. Chem.* 50: 1017-1025.

Nie et al. (1997) "Probing Single Molecules and Single Nanoparticles by Surface-Enhanced Raman Scattering" *Science* 275: 1102-1106.

Olive (2004) "Quantitative methods for analysis of protein phosphorylation in drug development" *Expert Rev. Proteomics* 1(3): 89-102.

Pienta et al. (2006) "Epidemiology of prostate cancer: molecular and environmental clues." *Urology* 48(5): 676-683.

Raman (1928) "A Change of Wave-length in Light Scattering" *Nature* 121: 619-619.

Rehault et al. (2002) "Design of new and sensitive fluorogenic substrates for human kallikrein hK3 (prostate-specific antigen) derived from semenogelin sequences." *Biochim. Biophys. Acta* 1596: 55-62.

Rittenhouse et al. (1998) "Human Kallikrein 2 (hK2) and prostate-specific antigen (PSA): two closely related, but distinct, kallikreins in the prostate." *Crit. Rev. Clin. Lab. Sci.* 35(4): 275-368.

Robert et al. (1997) "Characterization of prostate-specific antigen proteolytic activity on its major physiological substrate, the sperm motility inhibitor precursor/semenogelin I." *Biochemistry* 36(13): 3811-3819.

Wu et al. (2004) "Immunopeptidometric Assay for Enzymatically Active Prostate-Specific Antigen" *Clin. Chem.* 50: 125-129.

Wu et al. (2004) "Separation of enzymatically active and inactive prostate-specific antigen (PSA) by peptide affinity chromatography." *Prostate* 58: 345-353.

Yousef et al. (2001) "The New Human Tissue Kallikrein Gene Family: Structure, Function, and Association to Disease" *Endocr. Rev.* 22: 184-204.

* cited by examiner

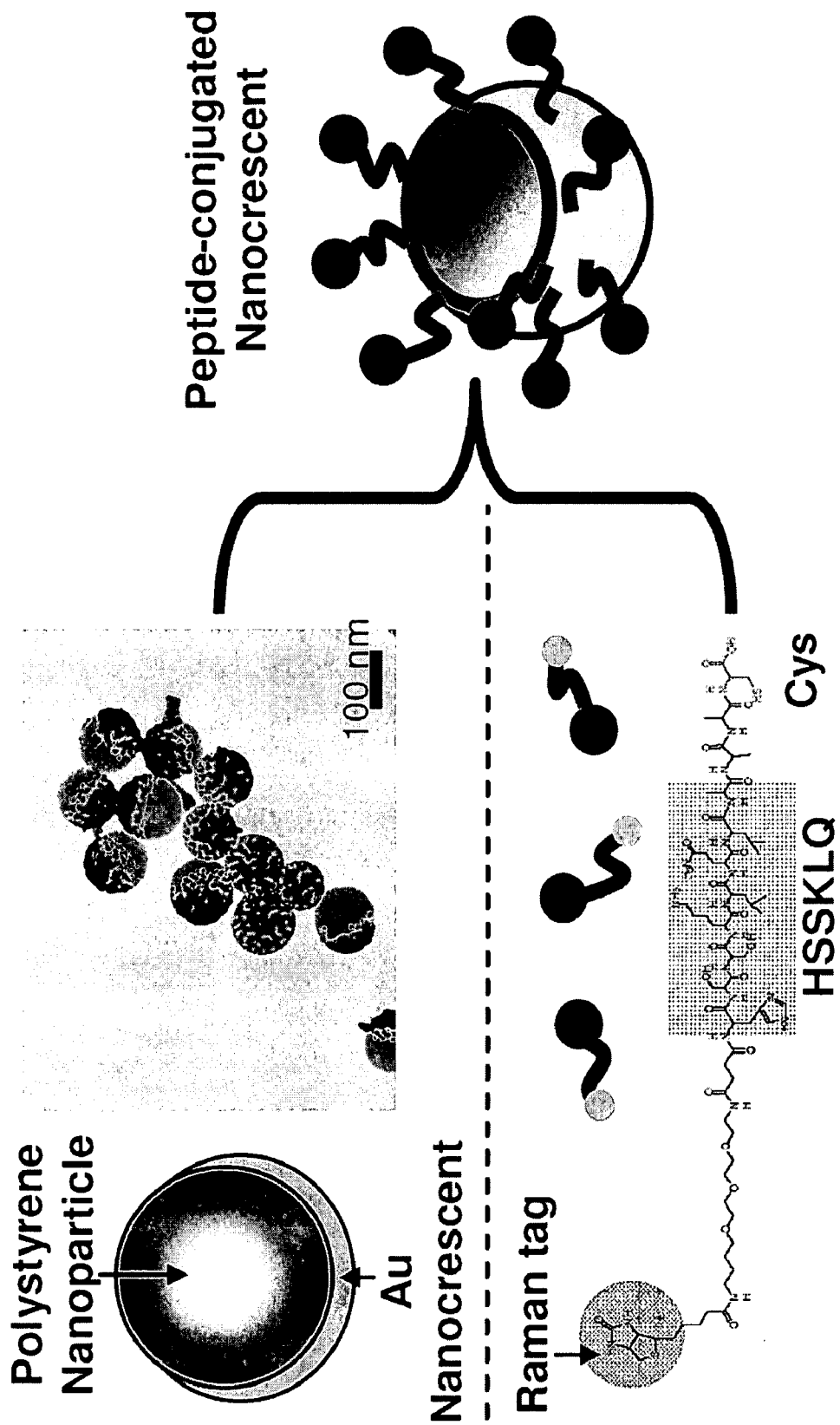

US 8,361,932 B2

DETECTION OF PROTEASE AND PROTEASE ACTIVITY USING A SINGLE NANOSCRESCENT SERS PROBE

CROSS-REFERENCE TO RELATED APPLICATIONS

This application is a 371 National Phase of PCT/US2007/010722, filed on May 2, 2007, which claims benefit of and priority to USSN 60/797,525, filed on May 3, 2006, both of which are incorporated herein by reference in their entirety for all purposes.

STATEMENT AS TO RIGHTS TO INVENTIONS MADE UNDER FEDERALLY SPONSORED RESEARCH AND DEVELOPMENT

This work was supported by DARPA, NIH Grant R1CA95393, UCSF Prostate Cancer SPORE award (NIH Grant P50 CA89520), and P01 CA72006. This work was performed in part under the auspices of the U.S. Deptartment. of Energy, at the University of California/Lawrence Berkeley National Laboratory under Contract no. DE-AC02-05CH11231. The Government of the United States of America has certain rights in this invention.

FIELD OF THE INVENTION

The present invention relates to the fields of Surface Enhanced Raman Scattering (SERS) using nanoprobes for detection of proteases. The present invention relates specifically to the detection of Prostate Specific Antigen (PSA) and proteolytically active PSA for diagnostic applications in prostate cancer.

BACKGROUND OF THE INVENTION

Prostate cancer is the most common cancer in men in Europe and North America (Crawford (2003) *Urology* 62: 3-12; Gronberg et al. 92003) *Lancet* 361: 859-864; Pienta et al. (2006) *Urology* 48: 676-683). One of the clinical diagnosis tools for prostate cancer is the measurement of plasma protein concentration of the prostate-specific antigen (PSA or hK3), which is a member of the large kallikrein (hK) protease family (for reviews, see, e.g., Yousef and Diamandis (2001) *Endocr. Rev.*, 22: 184-204; Denmeade and Isaacs (2002) *Nat. Rev. Cancer* 2: 389-396; Denmeade and Isaacs (2004) *BJU Int* 93 Suppl 1: 10-15) normally secreted from prostate luminal epithelial cells. Unlike other kallikrein family members, PSA is a chymotrypsin-like serine protease (Robert et al. (1997) *Biochemistry* 36: 3811-3819). In prostate cancer, PSA, aided by the proteolytic activity, is involved in tissue remodeling against the extracellular matrix, contributing critical control mechanisms to tumor invasion or progression. Other proteases play similar roles in cancers as well.

The introduction of plasma PSA screening since the 1980s has greatly improved the diagnosis, staging, and management of prostate cancer (Denmeade and Isaacs (2002) *Nat. Rev. Cancer* 2: 389-396); however, measurement of plasma PSA concentration does not differentiate the prostate cancer patients from those with benign prostatic hyperplasia, leading to a high false positive rate, requirement for more expensive biopsies, and even unnecessary surgical procedures (Denmeade and Isaacs (2004) *BJU Int* 93 Suppl 1: 10-15; Robert et al. (1997) *Biochemistry* 36: 3811-3819). Efforts to enhance the clinical value of the PSA for early detection of prostate cancer have included the characterization of various molecular isoforms of PSA (Mikolajczyk et al. (2004) *Clin. Chem.*, 50: 1017-1025; Mikolajczyk and Rittenhouse (2003) *Keio J. Med.* 52: 86-91; Mikolajczyk et al. (2004) *Clin. Biochem.* 37: 519-528). Among those various isoforms, the proteolytically active subpopulation of PSA is accepted as a more useful tumor marker and malignancy predictor than the serum PSA concentration (Wu et al. (2004) *Prostate* 58: 345-353; Wu et al. (2004) *Clin. Chem.*, 50: 125-129). Simple detection of the presence of PSA by a traditional immunostaining method can not reveal the proteolytic activity of PSA; therefore, it is of great importance to develop new methods to discriminate the proteolytically active isoform. Seminal fluid has been demonstrated to carry an abundance of proteolytically active PSA and is a biological source of PSA for protease activity assays (Brillard-Bourdet et al. (2002) *Eur. J. Biochem.*, 269: 390-395; Rehault et al. (2002) *Biochim. Biophys. Acta* 1596: 55-62). The concentration of proteolytically active PSA in seminal fluid is at 10-150 μM (Rehault et al. (2002) *Biochim. Biophys. Acta* 1596: 55-62), while its concentration in the plasma is much lower, from less than 0.1 nM in healthy individuals to higher than 1 nM in patients with prostate disease (Rittenhouse et al. (1998) *Crit. Rev. Clin. Lab. Sci.*, 35: 275-368). However, an assay that measures the proteolytic activity of PSA in seminal fluid or biopsy samples from fine needle aspiration is still not widely accepted, due to the quick decay of the proteolytic activity, and the limited amount of seminal fluid available from old patients or biopsy samples.

The sensitivity of current detection methods reach subnanomolar concentrations for PSA protein (Acevedo et al. (2002) *Clin. Chim. Acta* 317: 55-63; Charrier et al. (1999) *Electrophoresis* 20: 1075-1081; Bjartell et al. *Prostate Cancer P D* 2: 140-147) (mostly determined by the binding affinity of the antibody to PSA), and relatively large sample volume (milliliter) is required. However, the enzymatic assays have not enjoyed the same sensitivity enhancement.

SUMMARY OF THE INVENTION

In certain embodiments The present invention demonstrates the in vitro detection of proteases using a single peptide-conjugate nanocrescent surface enhanced Raman scattering (SERS) indicator (probe) with at least nanomolar sensitivity. This indicator enables detection of proteolytic activity in extremely small volumes. In certain embodiments, the detection volume is less than about 80 femtoliters, preferably less than about 50 femtoliters, more preferably less than about 40 or 30 femtoliters, and still more preferably less than about 20 or 15 femtoliters. In certain embodiments, the use of a highly focused excitation source allows the detection volume to be only about 10 femtoliter. In various embodiments the actual protease molecule number for the nanomolar samples is less than about 40 molecules, preferably less than about 40 molecules, more preferably less than about 30, 20, or 10 and in certain embodiments close to the single molecule level. Compared to other cancer biomarker detection assays, the present bioconjugated nanocrescent allows the detection of nanomolar concentrations of proteolytically active protease molecules in femtoliter volumes, which is crucial especially for cancer screening at a single cancer cell level.

One of the major advantages and applications of the small volume property is that it is useful in detecting proteases such as prostate-specific antigen (PSA) activity of cancer cells at single cell level. The small volume requirement and sensitivity level makes it possible to detect PSA activity in captured circulating prostate cancer cells for indications of metastasis, which is not feasible with conventional techniques. In semen, the PSA concentration is 10-150 µM, with approximately two thirds of the PSA enzymatically active. The sensitivity level achieved with the nanocrescent PSA probe (nanomolar range) is sufficient for a seminal fluid based assay, thus the nanocrescent SERS platform described herein is useful for clinical applications.

In certain embodiments the substrate is a nanocrescent surface enhanced Raman scattering (SERS) probe. The surface enhanced Raman scattering (SERS) probe is comprised of a peptide conjugated to a nanocrescent core and shell, wherein the probe features a sequence, that can be specifically cleaved by a protease (e.g., a protease recognition site), linked to a Raman active tag. Thus, this peptide-conjugated nanocrescent can be used as a specific screening tool to provide information on the presence, concentration and proteolytic activity of one or more proteases including, but not limited to various cancer biomarkers, such as prostate-specific antigen (PSA) in a biological sample.

In one embodiment, the nanocrescents comprise a core and a shell, having a peptide conjugated or tethered to the surface of the nanocrescent. The peptides comprise substrates specifically recognized and cleaved by the corresponding proteases to be detected.

In certain embodiments other peptide substrates specific for the protease can be used for the nanoprobe. There might be circumstances that substrate peptide with better kinetic properties can be used to accelerate the detection process. In one embodiment, other peptides with better specificity to PSA can also be used to detect PSA with better accuracy.

In various embodiments real-time reaction monitoring also provides information on protease activity rather than just measuring the presence of the protein. Different Raman tag molecules can be used and are successfully utilized in the Examples thereby demonstrating that detection of two or more types of cancer-related (or other) proteases can be carried out by multiplexing the peptide-conjugated nanocrescents. In certain embodiments the core can comprise magnetic material to allow spatial addressing of individual nanoparticles.

In certain embodiments different peptide substrates orthogonal to each other, or with minor overlap in specificity, can be used to detect the corresponding proteases. The peptide library can be conjugated to the nanocrescent probes and spatially separated in either a random array or ordered microarray format. The multiplexed array of the peptide-nanocrescent hybrid probes can be used to detect multiple proteases simultaneously.

The nanocrescent(s) can also be manipulated by laser or magnetic fields to address at high accuracy spatially (Liu et al. (2006) Nat Mater 5: 27-32), so that they can be multiplexed as high density arrays (with sub-microliter volume). In addition, the magnetic or laser maneuverability allow biosensing at desired locations (Liu et al. (2005) Adv. Mater. 17: 2683-2688), is useful for obtaining in situ measurements intracellularly.

In certain embodiments this invention provides an indicator (probe) for the detection of an active protease. The indicator typically comprises a nanocrescent attached to a peptide (substrate), where the peptide comprises a recognition site for the protease. In certain embodiments the indicator further comprises a Raman label attached to the peptide. Suitable Raman labels include, but are not limited to fluorophore, a chromophore, a quantum dot, a fluorescent microsphere, biotin, and the like. In certain embodiments the Raman label comprises a Rhodamine, a fluoresceine, or an exogenous chemical molecule. In certain embodiments the Raman label comprises a moiety selected from the group consisting of TRIT (tetramethyl rhodamine isothiol), NBC (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, 6-carboxy-X-rhodamine, azomethines, cyanines, xanthines, succinylfluoresceins, aminoacridine, and cyanide (CN), thiol (SH), chlorine (Cl), bromine (Br), methyl, phorphorus (P), sulfur (S), SN, Al, Cd, Eu, and Te. The Raman label can be attached directly to the peptide or through a linker. Similarly, the peptide can be attached directly to the nanocrescent or through a linker. In certain embodiments the nanocrescent comprises a shell without a core. In certain embodiments the nanocrescent comprises a core and a shell. In various embodiments the core comprises a material that provides a constant Raman spectrum (e.g., a plastic (e.g., polystyrene), a silica or other Group III, Group IV, or Group V material, a dextran, a magnetic material, and the like). In certain embodiments the nanocrescent comprises a metal selected from the group consisting of Ga, Au, Ag, Cu, Al, Ta, Ti, Ru, Ir, Pt, Pd, Os, Mn, Hf, Zr, V, Nb, La, Y, Gd, Sr, Ba, Cs, Cr, Co, Ni, Zn, Ga, In, Cd, Rh, Re, W, Mo, and oxides, and/or alloys, and/or mixtures, and/or nitrides, and/or sintered matrix thereof. In certain embodiments the nanocrescent has an outer radius that ranges from about 20 to about 800 nm. In certain embodiments the nanocrescent has an inner radius that ranges from about 10 nm to about 500 nm. In certain embodiments the nanocrescent is characterized by an inner radius r, and outer radius R, and a center to center distance between the center of the circle defined by the inner radius r and the outer radius R, where: r ranges from about 10 nm to about 500 nm; R ranges from about 20 nm to about 800 nm; and d ranges from about 5 nm to about 300 nm. In certain embodiments the nanocrescent is characterized by an inner radius r, and outer radius R, and a center to center distance between the center of the circle defined by the inner radius r and the outer radius R, where: r ranges from about 25 nm to about 500 nm; R ranges from about 20 nm to about 800 nm; and d ranges from about 5 nm to about 200 nm. In various embodiments the peptide comprises a recognition site for a protease selected from the group consisting of a serine protease, a metalloprotease, a cysteine protease, an aspartic acid protease, and a glutamic acid protease. In certain embodiments the peptide comprises a recognition site for a protease in an apoptosis pathway (e.g., a caspase). In certain embodiments the peptide comprises a recognition site for a caspase selected from the group consisting of caspase-8, caspase-9, caspase-3, caspase-6, and caspase-7. In certain embodiments the peptide comprises a recognition site for a thrombin. In certain embodiments the peptide comprises a recognition site for a serine protease. In certain embodiments the peptide comprises a PSA recognition site (e.g., HSSKLQ (SEQ ID NO:1)). In various embodiments the peptide ranges in length from 2 amino acids to 10, 20, or 30 amino acids. In certain embodiments the peptide is attached to the nanocrescent by a thiol group. In certain embodiments two different substrates (e.g., peptides) are attached to the nanocresent. In certain embodiments more than two different peptides are attached to the nanocresent. In certain embodiments the indicator is a component of a Raman active substrate.

In certain embodiments, this invention provides an indicator for the detection of an active nuclease. These indicators are essentially the same as the protease indicators described above, except the peptide (substrate) is replaced with a nucleic acid (e.g., a double stranded or single stranded nucleic acid). In certain embodiments the nucleic acid comprises a one or more nuclease recognition/cleavage sites (e.g., restriction sites).

In certain embodiments, the substrate (e.g., peptide, nucleic acid, sugar, carbohydrate, etc.) attached to the nanocrescent can comprise one or more binding sites (rather than cleavage sites) for the detection of, e.g., a cognate binding partner (e.g., receptor, nucleic acid binding protein, ligand, etc.).

Also provided are methods of detecting or quantifying the presence, amount, or activity of at least one protease in a sample. The method involve contacting the sample with an indicator comprising a nanocrescent attached to a peptide comprising a recognition site for a protease (e.g., as above); and monitoring differences in spectral characteristics of detected surface—Raman scattering spectra, the differences being indicators of the presence, amount or activity of protease present in the sample. In various embodiments the sample comprises a material selected from the group consisting of whole blood, a blood fraction, lymph, cerebrospinal fluid, oral fluid, mucus, urine, feces, bronchial lavage, ascites fluid, seminal fluid, bone marrow aspirate, pleural effusion, urine, and tumor cells or tissue. In various embodiments the indicator further comprises a Raman label attached to the peptide. Suitable Raman labels include, but are not limited to fluorophore, a chromophore, a quantum dot, a fluorescent microsphere, biotin, and the like. In certain embodiments the Raman label comprises a rhodamine, a fluoresceine, or an exogenous chemical molecule. In certain embodiments the Raman label comprises a moiety selected from the group consisting of TRIT (tetramethyl rhodamine isothiol), NBC (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, 6-Carboxy-X-rhodamine, azomethines, cyanines, xanthines, succinylfluoresceins, aminoacridine, and cyanide (CN), thiol (SH), chlorine (Cl), bromine (Br), methyl, phorphorus (P), sulfur (S), SN, Al, Cd, Eu, and Te. The Raman label can be attached directly to the peptide or through a linker. Similarly, the peptide can be attached directly to the nanocrescent or through a linker. In certain embodiments the nanocrescent comprises a shell without a core. In certain embodiments the nanocrescent comprises a core and a shell. In various embodiments the core comprises a material that provides a constant Raman spectrum (e.g., a plastic (e.g., polystyrene), a silica or other Group III, Group IV, or Group V material, a dextran, a magnetic material, and the like). In certain embodiments the nanocrescent comprises a metal selected from the group consisting of Ga, Au, Ag, Cu, Al, Ta, Ti, Ru, Ir, Pt, Pd, Os, Mn, Hf, Zr, V, Nb, La, Y, Gd, Sr, Ba, Cs, Cr, Co, Ni, Zn, Ga, In, Cd, Rh, Re, W, Mo, and oxides, and/or alloys, and/or mixtures, and/or nitrides, and/or sintered matrix thereof. In certain embodiments the nanocrescent has an outer radius that ranges from about 20 to about 800 nm. In certain embodiments the nanocrescent has an inner radius that ranges from about 10 nm to about 500 nm. In certain embodiments the nanocrescent is characterized by an inner radius r, and outer radius R, and a center to center distance between the center of the circle defined by the inner radius r and the outer radius R, where: r ranges from about 10 nm to about 500 nm; R ranges from about 20 nm to about 800 nm; and d ranges from about 5 nm to about 300 nm. In certain embodiments the nanocrescent is characterized by an inner radius r, and outer radius R, and a center to center distance between the center of the circle defined by the inner radius r and the outer radius R, where: r ranges from about 25 nm to about 500 nm; R ranges from about 20 nm to about 800 nm; and d ranges from about 5 nm to about 200 nm. In various embodiments the peptide comprises a recognition site for a protease selected from the group consisting of a serine protease, a metalloprotease, a cysteine protease, an aspartic acid protease, and a glutamic acid protease. In certain embodiments the peptide comprises a recognition site for a protease in an apoptosis pathway (e.g., a caspase). In certain embodiments the peptide comprises a recognition site for a caspase selected from the group consisting of caspase-8, caspase-9, caspase-3, caspase-6, and caspase-7. In certain embodiments the peptide comprises a recognition site for a thrombin. In certain embodiments the peptide comprises a recognition site for a serine protease. In certain embodiments the peptide comprises a PSA recognition site (e.g., HSSKLQ, SEQ ID NO:1). In various embodiments the peptide ranges in length from 2 amino acids to 10, 20, or 30 amino acids. In certain embodiments the peptide is attached to the nanocrescent by a thiol group. In certain embodiments two different substrates (e.g., peptides) are attached to the nanocresent. In certain embodiments more than two different peptides are attached to the nanocresent. In certain embodiments the indicator is a component of a Raman active substrate.

Also provide are libraries for the detecting the presence or activity of two or more active proteases. The libraries typically comprise a plurality of protease indicators the indicators comprising a nanocrescent attached to a peptide, e.g., as described above, where the peptide comprises a recognition site for the protease; where different nanocrescents have attached thereto different peptides so that different nanocrescents detect different proteases. In various embodiments the library is spatially addressed so that protease indicators specific for different proteases are localized at different locations on a substrate. In various embodiments the library is optically addressed so that protease indicators specific for different proteases produce different signals. In certain embodiments the library comprises at least 3 or more, preferably at least 10 or more, more preferably at least 20, 40, 80, or 100 or more different protease indicators. In certain embodiments the nanocrescents comprise magnetic cores and spatial segregation of the indicators is provided by magnetic fields. In certain embodiments the indicators are ionically or chemically coupled and/or adsorbed to a substrate.

Kits for the detection of an active protease are also provided. The kits typically include a container containing a nanocrescent attached to a peptide (e.g. as described herein), where the peptide comprises a recognition site for the protease. In certain embodiments the kit further comprises a Raman label attached to the peptide. In certain embodiments the kit further comprises instructional materials teaching the use of the indicator for the detection of the presence, concentration or activity of an active protease using surface enhanced Ramen scattering (SERS).

In certain embodiments this invention provides an indicator for the detection of an nuclease. The indicator comprises a nanocrescent (e.g., as described herein) attached to a single or double-stranded oligonucleotide, where the oligonucleotide comprises a recognition site for the nuclease. In certain embodiments the indicator further comprises a Raman label attached to the oligonucleotide.

Also provided are methods of detecting the presence or quantity of an analyte. The methods typically involve contacting a sample comprising the analyte to an indicator, the indicator comprising a nanocrescent attached to a substrate that is specifically or preferentially bound by the analyte in the presence of a Raman-labeled moiety that competes with the analyte for binding to the substrate; and detecting the Raman spectrum of the indicator where a change in the Raman spectrum produced by dissociation of the Raman-labeled moiety from the substrate provides a measure of the presence or quantity of the analyte in the sample. In certain embodiments the substrate is a peptide or a nucleic acid.

In certain embodiments, the peptide attached to the nanocrescent is not an antibody or an antibody fragment.

DEFINITIONS

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The term "active protease" refers to a protease that is in a form capable of cleaving (hydrolyzing) a peptide bond in the substrate for that protease when the protease is contacted with the substrate under conditions that support activity of that protease.

The term "nanocrescent" refers to nanoparticles whose cross-sectional profile resembles the crescent moon with sharp edges.

"Analyte," as used herein, is the substance to be detected in a test sample using the present invention. The analyte can be any substance, e.g. an enzyme for which there exists specific binding member e.g., a substrate or for which a specific binding member can be prepared, and the analyte can bind to one or more specific binding members in an assay. The term "analyte" also includes any enzymes, antigenic substances, haptens, antibodies, and combinations thereof. The analyte can include, but is not limited to a protein, a peptide, an amino acid, a carbohydrate, a hormone, asteroid, a vitamin, a drug including those administered for therapeutic purposes as well as those administered for illicit purposes, a bacterium, a virus, and metabolites of or antibodies to any of the above substances.

"Radiation," as used herein, is an energy in the form of electromagnetic radiation which, when applied to a test mixture, causes a Raman spectrum to be produced by the Raman-active label therein, and also causes the metal surface to support surface-enhanced Raman light scattering by the Raman-active labels, which become associated with the particulate surface.

A "Raman label", "Raman tag", or "Raman active label" is a substance that produces a detectable Raman spectrum, which is distinguishable from the Raman spectra of other components present, when illuminated with a radiation of the proper wavelength. Other terms for a Raman-active label can include dye and reporter molecule.

"Specific binding member," as used herein, is a member of a specific binding pair, i.e., two different molecules where one of the molecules, through chemical or physical means, specifically binds to the second molecule. In addition to antigen and antibody-specific binding pairs, other specific binding pairs include biotin and avidin, carbohydrates and lectins, complementary nucleotide sequences (including probe and captured nucleic acid sequences used in DNA hybridization assays to detect a target nucleic acid sequence), complementary peptide sequences, effector and receptor molecules, enzyme cofactors and enzymes, enzyme inhibitors and enzymes, and the like. Furthermore, specific binding pairs can include members that are analogs of the original specific binding member. For example a derivative or fragment of the analyte, i.e., an analyte-analog, can be used so long as it has at least one epitope in common with the analyte. Immunoreactive specific binding members include antigens, haptens, antibodies, and complexes thereof including those formed by recombinant DNA methods or peptide synthesis.

The term "test mixture," refers to a mixture of the test sample and other substances used to apply the present invention for the detection of analyte in the test sample. Examples of these substances include: Specific binding members, ancillary binding members, analyte-analogs, Raman-active labels, buffers, diluents, and particulates with a surface capable of causing a surface-enhanced Raman spectroscopy, and others.

The term "test sample," as used herein, means the sample containing the analyte to be detected and assayed using the present invention. The test sample can contain other components besides the analyte, can have the physical attributes of a liquid, or a solid, and can be of any size or volume, including for example, a moving stream of liquid. The test sample can contain any substances other than the analyte as long as the other substances do not interfere with the specific binding of the specific binding member or with the analyte or the analyte-analog. Examples of test samples include, but are not limited to: Serum, plasma, sputum, seminal fluid, urine, other body fluids, tissue and cell samples (e.g., tumor samples, organ samples, and the like) and environmental samples such as ground water or waste water, soil extracts and pesticide residues.

BRIEF DESCRIPTION OF THE DRAWINGS

FIGS. 1A, 1B, 1C illustrate a peptide-conjugated nanocrescent for PSA detection, a fabrication procedure, and detection. FIG. 1A: Fabrication procedure. The nanoscale Au layer was evaporated on polystyrene nanoparticles to form the Au nanocrescent as shown in the TEM image, with the crescent tip showing lighter density. Peptides were synthesized with the specific PSA substrate sequence HSSKLQ (SEQ ID NO:1) and were terminated by a Raman tag molecule, biotin or R19 (not shown), respectively, and cysteine for both versions of tagged peptides. The peptides were conjugated to the Au surface of the nanocrescents through an Au—S bond. FIG. 1B: PSA detection scheme. Before the proteolytic reaction, the SERS spectrum of the peptide-conjugated nanocrescent contains the characteristic peaks from the Raman tag molecules, polystyrene nanoparticle, and the peptides; after the digestion reaction by PSA, the peptide is cleaved after Q. The cleavage fragment containing the Raman tag molecules diffuses away from the nanocrescent surface, while the other fragment remains on the nanocrescent surface. The SERS spectrum of the peptide becomes different and the characteristic peaks from the Raman tag molecule disappear. FIG. 1C: (1) Simulated local electric field amplitude enhancement by nanocrescent. The tip region of the nanocrescent has an electromagnetic enhancement factor of 100 fold. (2) Polar electric field energy distribution on the nanocrescent. Almost 100% energy is concentrated near the tip area which accounts for ~⅙ of total area of the nanocrescent.

FIG. 2A: Conceptual schematics of a nanocrescent moon SERS substrate. The gold surface can be functionalized with biomolecular linker to recognize specific biomolecules. The sharp edge of the nanocrescent moon can enhance the Raman scattering intensity so that the biomolecules on it can be detected. FIG. 2B: Geometrical schematics of a nanocrescent moon. A gold nanocrescent moon with sharp edges integrates the geometric features of nanoring and nanotips. FIG. 2C: Transmission electron microscope images of two nanocrescent moons. Shown nanocrescent moons are both of 300 nm inner-diameter, 100 nm-bottom-thickness, but with different orientations. The scale bars are 100 nm.

FIG. 7A: SERS spectra in the peptide digestion by 420 nM PSA with biotin as the Raman tag molecule. FIG. 7B: SERS spectra in the peptide digestion by 420 nM PSA with R19 as the Raman tag molecule. FIG. 7C: SERS spectra in the peptide digestion by 420 nM PSA in the presence of inhibitor with R19 as the Raman tag molecule. FIG. 7D: SERS spectra in the peptide digestion by 420 nM Granzyme B with R19 as the Raman tag molecule.

FIG. 8A: Raman peak intensities of biotin at 525 $cm^{-1}$ in the digestion reactions with 0 M (buffer solution), 4.2 nM, 42 nM and 420 nM PSA, respectively. FIG. 8B: Raman peak intensities of R19 at 1183 $cm^{-1}$ in the digestion reactions with 420 nM PSA, 420 nM PSA with inhibitor, and 420 nM Granzyme B, respectively.

DETAILED DESCRIPTION

In various embodiments, this invention pertains to novel indicators that provide a measure of the presence and/or quantity and/or activity of one or more proteases in a sample. In certain embodiments the indicators comprise one or more nanocrescent structures attached to substrate(s) (e.g., polypeptide(s)) for one or more protease molecules see, e.g., FIG. 1A). The indicators can, optionally, further comprise one or more Raman tags attached to the substrate. The indicators function as extremely sensitive probes for Raman scattering detection systems (e.g. surface enhanced Raman scattering (SERS) probes).

In certain embodiments the present invention pertains to the in vitro, in situ, or, in certain instances in vivo, detection of proteolytically active biological molecules using a peptide-conjugate nanocrescent surface enhanced Raman scattering (SERS) probe. The probes described herein can achieve at least nanomolar sensitivity, thereby enabling detection of proteolytic (or other biological) activity in extremely low concentrations (e.g., one or several molecules) and/or in extremely small volumes (e.g., femtoliter volumes). In various embodiments, the nanoscale dimension of the indicator(s) and the high local electromagnetic field enhancement of the indicator (FIG. 1C) enables high-sensitivity optical detection of biomolecular reactions on its surface.

In certain preferred embodiments, the indicator comprises a nanocrescent surface enhanced Raman scattering (SERS) probe. The surface enhanced Raman scattering (SERS) probe is can comprise a peptide conjugated to a nanocrescent structure (e.g., a nanocrescent core and shell), where the peptide contains a specific amino acid sequence that is recognized and cleaved by a protease (a protease recognition site). In various embodiments the peptide is attached to a Raman tag. Cleavage of the peptide by the "target" protease provides a strong change in the Raman spectrum that is readily detected. Thus, the peptide-conjugated nanocrescent can be used as a specific screening tool to provide information on the presence, concentration and proteolytic activity of the one or more proteases, e.g., cancer biomarkers, such as prostate-specific antigen (PSA) in a biological sample.

Nanocrescent Composition and Fabrication.

The indicators of the present invention typically comprise one or more nanocrescents coupled to a biological molecule, preferably a peptide. In certain embodiments the nanocrescents can comprise a core and a shell. When present, the core can be comprised of a plastic (e.g., polystyrene), silica or other mineral, or other Group III, Group IV, or Group V material, a dextran, a magnetic material, or any other materials with a substantially constant Raman spectra.

Figure 2A:
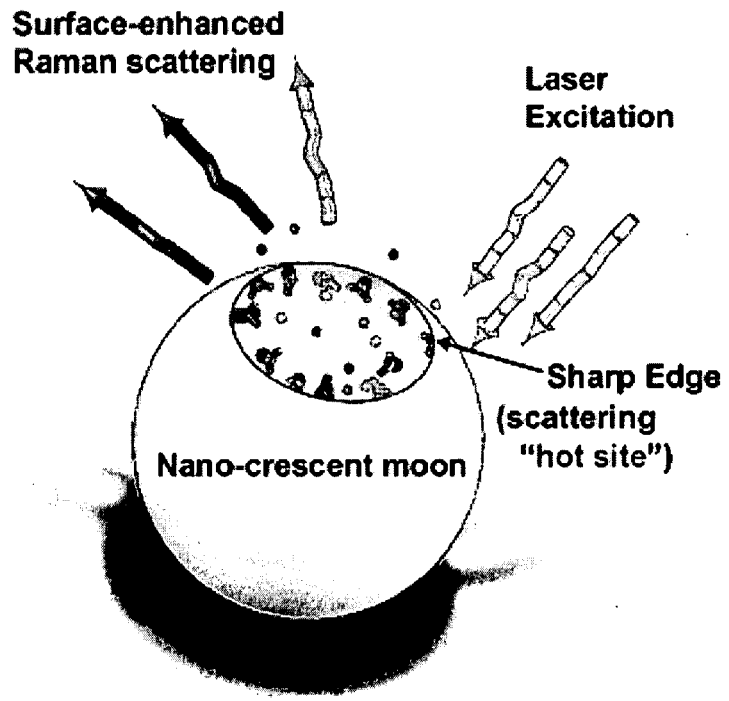
FIGS. 2A, 2B, and 2C illustrate Gold nanocrescent moons with sharp edges.
Figure 2B:
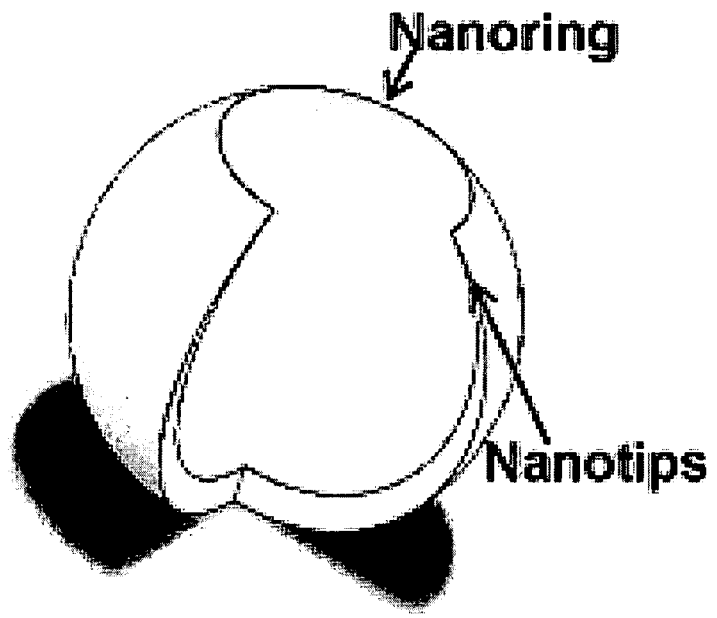

The nanocrescent "moon" structures have features of both nanotips and nanorings which allows local electromagnetic field enhancement (FIG. 2A). In cross-sectional view, the shape of the nanocrescent moon resembles a crescent nanomoon with sharp tips, so the sharp edge of the nanocrescent moon has the rotational analogy to a sharp tip and it expands the SERS "hot site" from a tip to a circular line (i.e., a group of nanotips) as shown in FIG. 2B. From a top view the shape of the nanocrescent moon resembles a nanoring with a higher sharpness than previously demonstrated nanorings (Aizpurua et al. (2003) *Phys. Rev. Lett.* 90: 057401), so the circular sharp edge of the nanocrescent moon can have a stronger field emitting or "antenna" effect.

Figure 2C:
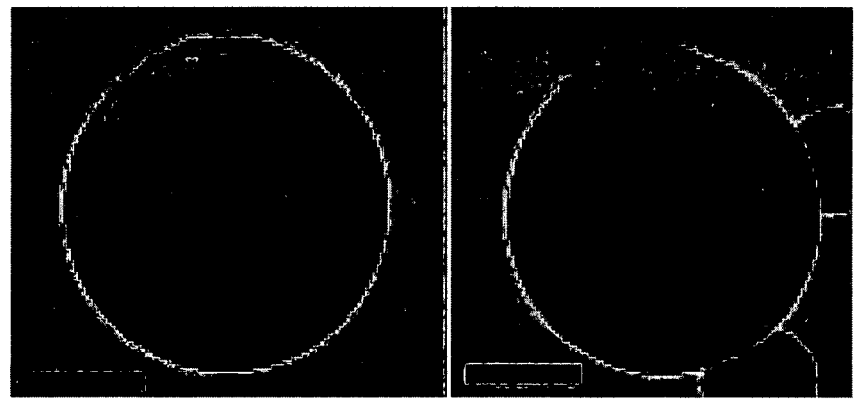

In various embodiments the gold nanophotonic crescent moons have sub-10 nm sharp edges as shown in FIG. 2C.

Figure 4:
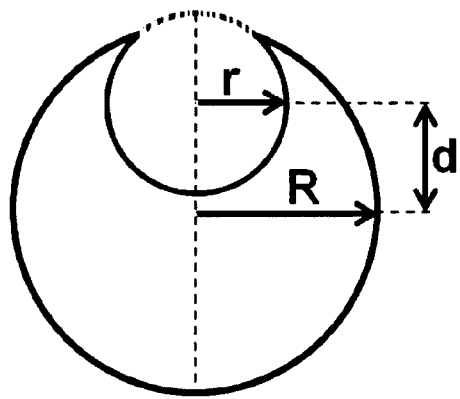
FIG. 4 illustrates the geometry of a nanocrescent moon where r is the inner radius, R is the outer radius, and d is the center-center distance as shown as two partially overlapping circles.

In certain embodiments the nanocrescents can be characterized by a geometry as illustrated in FIG. 4, where r is the inner radius, R is the outer radius, and d is the center-center distance as shown as two partially overlapping circles. In various embodiments R ranges from about 20 nm to about 800 nm, preferably from about 40 nm to about 600 nm, more preferably from about 50 nm to about 500 or 400 nm, and most preferably from about 100 nm to about 200 nm 300 nm. In various embodiments, r ranges from about 10 nm to about 500 nm, preferably from about 20 nm to about 400 nm, more preferably from about 50 nm to about 300 nm, and most preferably from about 100 nm to about 200 nm. In various embodiments d ranges from about 10 to about 400 nm, preferably from about 20 nm to about 200 nm or 300 nm, more preferably from about 30 nm, 40 nm or 50 nm to about 100 or 150 nm.

The nanocrescent shell can be comprised of a metal (e.g., gold, silver, tungsten, platinum, titanium, iron, manganese, and the like, or oxides or alloys thereof), a semiconductor material, multi-layers of metals, a metal oxide, an alloy, a polymer, carbon nanomaterials, and the like. In certain embodiments the nanocrescent shell comprises one or more of the following: tungsten, tantalum, and niobium, Ga, Au, Ag, Cu, Al, Ta, Ti, Ru, Ir, Pt, Pd, Os, Mn, Hf, Zr, V, Nb, La, Y, Gd, Sr, Ba, Cs, Cr, Co, Ni, Zn, Ga, In, Cd, Rh, Re, W, Mo, and oxides, alloys, mixtures, and/or nitrides thereof.

In various embodiments the core ranges from about 30 nm to about 500 nm, preferably about 50 nm to about 200 nm, 300 nm, or 400 nm, more preferably from about 50 nm to about 100 nm or 150 nm in diameter, and the shell is preferably 3 nm to about 80 nm, more preferably about 5 nm to about 50 nm, still more preferably about 8 nm to about 20 or 30 nm, and most preferably about 10 nm to about 20 nm or 25 nm. By choosing different core size and shell thickness, the plasmon resonance wavelength and the surface enhancement factor can be tuned to match various applications.

Figure 3:
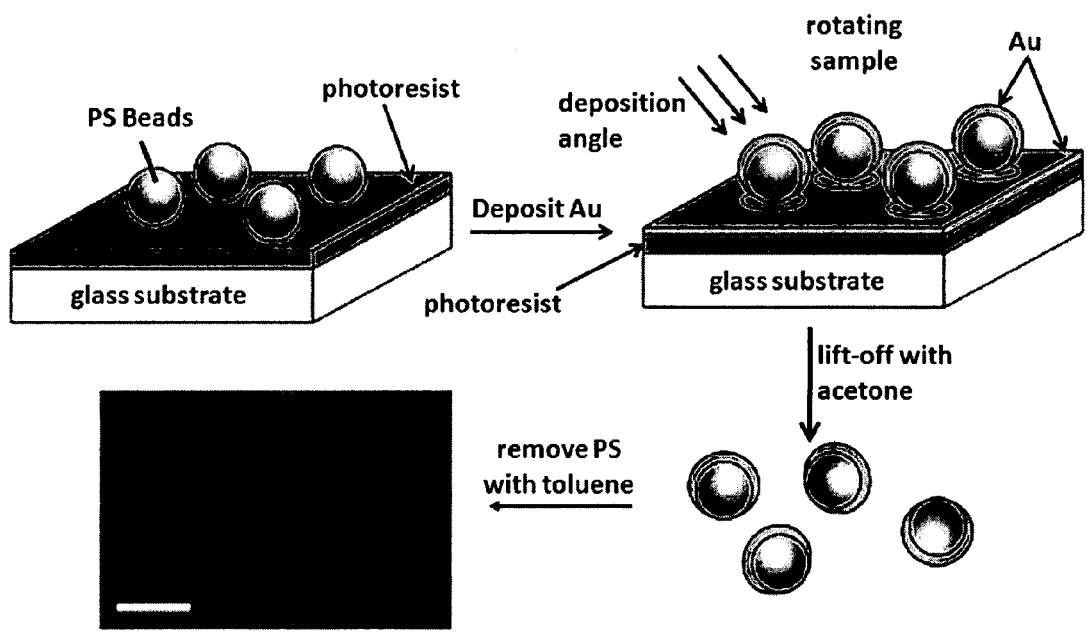
FIG. 3 illustrates a fabrication procedure for nanocrescent moons. (a) Casting a monolayer of spherical polystyrene colloids on a photoresist coated glass substrates. (b) Coating a gold layer on the surfaces of polystyrene colloids by electron beam evaporation. The sample is kept rotating at a certain angle with respect to the gold target during deposition. The shape of the nanocrescent moons depends on the deposition angle in addition to the size of the polystyrene spheres. (c) Lift-off of the gold-coated polystyrene spheres from the substrate. (d) Scanning electron microscopy of gold nanocrescent moons. The dissolution of the colloidal particles releases the nanocrescent moons into a suspension. The nanocrescent moons are then collect and placed on a substrate. For the convenience of demonstration in SEM, the shown nanocrescent moons were not subject to dilution in water like the nanocrescent moons used in our optical experiments. The scale bar is 200 nm.

FIG. 1A schematically illustrates one embodiment of a nanocrescent indicator of the present invention and provides an electron micrograph thereof. In certain embodiments the nanocrescents are preferably fabricated by angled deposition of the nanocrescent material(s) (e.g., silver, gold, etc.) on a rotating nanoparticle (e.g., polystyrene nanoparticle template) as described by Lu et al. (2005) *Nano Lett* 5, 119-124, which is incorporated herein by reference. The fabrication procedure is schematically illustrated in FIG. 3. As shown in FIG. 3, this method involves casting a monolayer of spherical core materials (e.g., polystyrene colloids) on photoresist-coated substrates (e.g., glass substrates). The nanocrescent shell material(s) (e.g., gold, silver, etc.) are coated on the surfaces of the cores by electron beam evaporation. The sample is kept rotating at a certain angle with respect to the gold (or other material) target during deposition. The shape of the nanocrescent moons depends on the deposition angle in addition to the size of the core structures (e.g., polystyrene spheres). The coated nanocrescents can be lifted from the substrate using an appropriate solvent (e.g., acetone). The cores can, optionally, be removed from the nanocrescents, by the use of appropriate solvent(s) (e.g., toluene). The nanocrescent moons can then be collected and placed on a substrate.

In one illustrative embodiments, the nanocrescents comprise a 100 nm polystyrene core and a 10~20 nm gold crescent shell. The nanoscale Au layer is evaporated on polystyrene nanoparticles to form the Au nanocrescent as shown in the TEM image in FIG. 1C, with the crescent tip showing lighter density. In certain embodiments the nanoparticle core is not removed and serves as the internal control in the SERS detections.

This fabrication procedure is illustrative and not limiting. Using the teachings provided herein, variations of the present protocols and other nanocrescent fabrication methods will be recognized by one of skill in the art.

Protase Substrates

The nanocrescent indicators described herein can utilize polypeptide sequences comprising one or more recognition site(s) for any protease(s) it is desired to detect. Proteases (proteolytic activity) are not only required for maintenance of normal cellular functions but are also central to the pathogenesis of a variety of human diseases. Parasitic (for example schistosomiasis and malaria), fungal (such as *C. albicans*) and viral infections (for example HIV, herpes and hepatitis), and also cancer, inflammatory, respiratory, cardiovascular and neurodegenerative diseases, including Alzheimer's, require proteolytic activity for progress. Detection of protease presence, quantity, or activity is thus useful as a diagnostic/prognostic marker for the presence or likelihood of disease. In addition, detection of protease activity (or the inhibition thereof) is useful in screening for protease inhibitor therapeutics for the treatment of a number of pathologies.

A "protease" that can be detected and/or quantified according to the invention is an enzyme that typically hydrolyzes a peptide bond between a pair of amino acids located in a polypeptide chain, also called an endoprotease. Proteases are typically defined by reference to the nucleophile in the catalytic center of the enzyme. The most common nucleophiles arise from the side chains of serine, aspartic acid, and cysteine, resulting in families of proteases, such as serine proteases (Paetzel et al. (1997) *Trends Biochem. Sci.* 22: 28-31), aspartyl proteases (Spinelli et al. (1991) *Biochemie* 73: 1391-1396), and cysteine proteases (Altschuh et al. (1994) *Prot. Eng.* 7: 769-75, 1994). Metalloproteases usually contain a zinc catalytic metal ion at the catalytic site (Klimpel et al. (1994) *Mol. Microbiol.* 13: 1093-1100). Illustrative examples of members of each of these protease families are provided in Table 1.

TABLE 1

Illustrative proteases and protease recognition sites
(* indicates the peptide bond being hydrolyzed).

| Protease Family | Protease | Protease Recognition Sites | SEQ ID NO |
|---|---|---|---|
| serine | factor Xa | Ile-Gly-Gly-Arg* | 2 |
| serine | trypsin | Lys*, Arg* | |
| serine | chymotrypsin | Tyr*, Phe*, Leu*, Ile*, Val*, Trp*, and His* at high pH | |
| serine | thrombin | Arg* | |
| serine | PSA | | 3 |
| serine and cysteine variants | peanut mottle polyvirus Nla protease | Glu1-Xaa-Xaa-Tyr-Gln*(Ser/Gly) | 4 |
| cysteine | papaine | Arg*, Lys*, Phe* | |

TABLE 1-continued

Illustrative proteases and protease recognition sites
(* indicates the peptide bond being hydrolyzed).

| Protease Family | Protease | Protease Recognition Sites | SEQ ID NO |
|---|---|---|---|
| cysteine | bromelaine | Lys*, Ala*, Tyr*, Gly* | |
| cysteine | cathepsin B | Arg*Arg, | 5 |
| | | Phe*Arg | 6 |
| cysteine | cathepsin L | Phe*Arg | 6 |
| aspartyl | HIV protease | Phe*Pro | 7 |
| aspartyl | S. cerevisiae yapsin 2 | Lys*, Arg* | |
| aspartyl | cathepsin D | Phe*Phe | 8 |
| | | Phe*Lys | 9 |
| | | Leu*Phe | 10 |
| | | Leu*Tyr | 11 |
| metallo- | thermolysin | *Tyr, *Phe, *Leu, *Ile, *Val, *Trp and *His | |
| metallo- | peptidyl-Lys metalloendopeptidase | Xaa*Lys | 12 |
| metallo- | peptidyl-Asp metallodndopeptidase | Xaa*Asp | 13 |
| | | Xaa*Glu | 14 |
| | | Xaa*Cys | 15 |
| metallo- | coccolysin | *Leu, *Phe, *Tyr, *Ala | |
| metallo- | autolysin | Leu-Trp-Met*Arg-Phe-Ala | 16 |
| metallo- | gelatinase A (MMP-2) | Pro-Gln-Gly*Ile-Ala-Gly-Gln | 17 |
| metallo- | human neutrophil collagenase (MMP-8) | Gly-Leu-Ser-Ser-Asn-Pro*Ile-Gln-Pro | 18 |

A "protease recognition site" is a contiguous sequence of amino acids connected by peptide bonds that contains a pair of amino acids which is connected by a peptide bond that is hydrolyzed by a particular protease. Optionally, a protease recognition site can include one or more amino acids on either side of the peptide bond to be hydrolyzed, to which the catalytic site of the protease also binds (Schecter and Berger, (1967) Biochem. Biophys. Res. Commun. 27: 157-62), or the recognition site and cleavage site on the protease substrate can be two different sites that are separated by one or more (e.g., two to four) amino acids.

The specific sequence of amino acids in the protease recognition site typically depends on the catalytic mechanism of the protease, which is defined by the nature of the functional group at the protease's active site. For example, trypsin hydrolyzes peptide bonds whose carbonyl function is donated by either a lysine or an arginine residue, regardless of the length or amino acid sequence of the polypeptide chain. Factor Xa, however, recognizes the specific sequence Ile-Glu-Gly-Arg (SEQ ID NO:19) and hydrolyzes peptide bonds on the C-terminal side of the Arg.

Thus, in various embodiments, a protease recognition site can comprise at least 2, 3, 4, 5, 6, 7, 8, 9, or 10 or more amino acids. Optionally, additional amino acids can be present at the N-terminus and/or C-terminus of the recognition site. A protease recognition site according to the invention also can be a variant of a recognition site of a known protease as long as it is recognized/cleaved by the protease.

Various preferred protease recognition sites include, but are not limited to protease recognition sites for proteases from the serine protease family, or for metalloproteases, or for a protease from the cysteine protease family, and/or the aspartic acid protease family, and/or the glutamic acid protease family. In certain embodiments preferred serine proteases recognition sites include, but are not limited to recognition sites for chymotrypsin-like proteases, and/or subtilisin-like proteases, and/or alpha/beta hydrolases, and/or signal peptidases. In certain embodiments preferred metalloprotease recognition sites include, but are not limited to recognition sites for metallocarboxypeptidases or metalloendopeptidases.

Protease recognition sites are well known to those of skill in the art. Recognition sites have been identified for essentially every known protease. Thus, for example, recognition sites (peptide substrates) for the caspases are described by Earnshaw et al. (1999) Annu. Rev. Biochem., 68: 383-424, which is incorporated herein by reference (see also Table 2).

TABLE 2

Illustrative peptide substrates for caspases (* indicates the peptide bond being hydrolyzed).

| Name | Peptide Substrate | SEQ ID NO |
|---|---|---|
| Caspase I (ICE) | YEVD*X | 20 |
| | WEHD*X | 21 |

TABLE 2-continued

Illustrative peptide substrates for caspases (* indicates the peptide bond being hydrolyzed).

| Name | Peptide Substrate | SEQ ID NO |
|---|---|---|
| Caspase 2 (Ich-I$_L$) | VDVAD*X<br>DEHD*X | 22<br>23 |
| Caspase 3 (CPP32,. Apopain) | DMQD*X<br>DEVD*X | 24<br>25 |
| Caspase 4 (Ice$_{rel}$II Tx, Ich-2) | LEVD*X<br>(W/L)EHD*X | 26<br>27 |
| Caspase 5 (ICErelIII, Ty) | (W/L)EHD*X | 28 |
| Caspase 6 (Mch2) | VEID*N<br>VEHD*X | 29<br>30 |
| Caspase 7 (Mch3, CMH-1, ICE-LAP3) | DEVD*X | 31 |
| Caspase 8 | IETD*X<br>LED*X | 32<br>33 |
| Caspase 9 | LEHD*X | 34 |
| Caspase 10 | IEAD*X | 35 |

In one illustrative embodiment to detect PSA, the peptide design incorporates the amino acid sequence of the active site of PSA-specific peptides with serine residues and flanking sequences that can be recognized by PSA. Thus, for example, in one embodiment, the peptide contains the sequence HSSKLQ-LAAAC (SEQ ID NO:36) which has been shown to have very high specificity for proteolytically active PSA. (see, e.g., Denmeade, et al. (1997) *Cancer Res* 57: 4924-4930). It has been shown that HSSKLQ-L (SEQ ID NO:37) is cleaved by PSA but not by any other proteases in vivo in a mouse mode (Denmeade et al. (2003) *J. Natl. Cancer Inst.* 95: 990-1000). Thus, in another embodiment, multiple peptides can be generated, each having a random or known sequence portion, so long as each incorporates the specific sequence of HSSKLQ-LAAAC (SEQ ID NO:36) or HSSKLQ-L (SEQ ID NO:37).

In one illustrative embodiment, the PSA digestion site is between the Glutamine (Q) and Leucine (L) residues in the peptide HSSKLQ-LAAAC (SEQ ID NO:36). The peptides are digested into 2 fragments, HSSKLQ (SEQ ID NO: 1) and LAAAC (SEQ ID NO:38). The peptide is preferably attached to the nanocrescent surface, such that the peptide is not sterically hindered from the PSA enzyme and thereby optimally accessible. It is contemplated that an additional spacer positioned between the substrate peptide sequence HSSKLQ-LAAAC (SEQ ID NO:36) and the Cys (C) residue, can improve the presentation of PSA substrate peptide HSSKLQ (SEQ ID NO:1) on the surface and thereby increase the detection sensitivity. Although by doing so the distance of the Raman tag molecules could be farther from the nanocrescent surface resulting in a lower Raman intensity level. However, the coil-like short peptide structure results in a large probability of the distal Raman tag molecule to contact the nanocrescent surface.

In certain embodiments the peptide comprises at least one protease recognition site. In various embodiments the peptide can comprise two, three or more protease recognition sites. The sites can be for the same protease and have different motifs all of which are recognized by that protease. In certain embodiments the sites can be identical. In certain embodiments the peptide can comprise multiple recognition sites, each for a different protease thereby allowing detection or quantification of the presence or activity of any one of several proteases.

Typically, the peptide will be of sufficient length to incorporate the desired protease recognition site(s). In certain embodiments the peptide will be longer than the protease recognition sites and contain additional amino acid residues, e.g., to act as spacers and/or facilitate recognition by the protease. Typically, the peptide will range in length from any of about 2, 3, 4, 5, 6, 8, or 10 amino acids to any of about 20, 30, 50, 80, or 100 amino acids. In certain embodiments the substrate peptide is an oligopeptide about 3-12, or about 4-12, or about 6-12, or about 8-12, or about 10-12 amino acid residues in length. However, in certain embodiments the peptide can be as short as 4 amino acid residues, and as long as 100 amino acids.

Raman Tags

In various embodiments, one or more Raman labels (Raman tags) can be attached to the substrate (e.g., polypeptide) that is attached to the nanocrescent(s). The presence of such Raman tags can enhance the change in Raman signal produced by cleavage of the peptide.

A variety of Raman labels are known in the art (e.g., U.S. Pat. Nos. 5,306,403; 6,002,471; 6,174,677, which are incorporated herein by reference) and any such known Raman label(s) can be used. The labels typically have characteristic (e.g., unique) and highly visible/detectable optical signatures. Non-limiting examples of tag molecules include TRIT (tetramethyl rhodamine isothiol), NBC (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, 6-carboxy-X-rhodamine, azomethines, cyanines, xanthines, succinylfluoresceins, aminoacridine, and cyanide (CN), thiol (SH), chlorine (Cl), bromine (Br), methyl, phorphorus (P), sulfur (S), SN, Al, Cd, Eu, Te, and compounds containing such moieties. In certain embodiments, carbon nanotubes, quantum dots (see, e.g., Evident Technologies, Troy N.Y.; Invitrogen/Molecular Probes, etc.), or microspheres (e.g. fluorescent microspheres (see, e.g., Transfluosphres® from Invitrogen/Molecular Probes) can be used as Raman tags.

Many Raman labels are commercially available (e.g., from Invitrogen/Molecular probes) and are often provided attached to linkers, and/or derivatized with one or more functional groups to facilitate coupling to other moieties.

Coupling of Substrate to Nanocrescent

The peptide (protease substrate) and/or when present the Raman label(s) can be coupled to each other by any of a number of methods known to those of skill in the art. The peptide (or other substrate) can be coupled directly to the nanocrescent(s), e.g., through a reactive group on the substrate (peptide) and/or the nanocrescent(s). or the peptide (or other substrate) can be attached to the nanocrescent(s) through a linker.

Similarly, when present, the Raman label(s) can be attached to the peptide (or other substrate) directly (e.g., through a functional group) or through a linker as well.

For example, in certain embodiments the substrate peptide is tethered onto the surface of a gold nanocrescent shell using the cysteine group at the carboxyl terminus of the peptide to attach the peptide to the gold surface, relying on the gold-thiol reaction to form a covalent bond. In various embodiments the nanocrescent (e.g., Au) surface and/or the substrate (e.g., protease substrate) can derivatized with, for example, amine, carboxyl groups, alkyl groups, alkyene groups, hydroxyl groups, or other functional groups so the peptide (or other substrate) can be linked directly to the nanocrescent surface and/or Raman label(s) or coupled through a linker. In another embodiment, the nanoparticles can be coated with, e.g. silica shells with amine, carboxyl, or other functional groups for attachment to the peptide (or other substrate).

Suitable linkers include, but are not limited to hetero- or homo-bifunctional molecules that contain two or more reactive sites that may each form a covalent bond with the respective binding partner (i.e., Raman tag, peptide (or other substrate), nanocrescent surface or functional group thereon, etc.). Linkers suitable for joining such moieties are well known to those of skill in the art. For example, a protein molecule can readily be linked by any of a variety of linkers including, but not limited to a peptide linker, a straight or branched chain carbon chain linker, or by a heterocyclic carbon linker. Heterobifunctional cross-linking reagents such as active esters of N-ethylmaleimide have been widely used to link proteins to other moieties (see, e.g., Lerner et al. (1981) *Proc. Nat. Acad. Sci.* (USA), 78: 3403-3407; Kitagawa et al. (1976) *J. Biochem.*, 79: 233-236; Birch and Lennox (1995) Chapter 4 in Monoclonal Antibodies: Principles and Applications, Wiley-Liss, N.Y., and the like).

In certain embodiment, the nanocrescent and/or the Raman label can be joined to the peptide (or other substrate) utilizing a biotin/avidin interaction. In certain embodiments biotin or avidin, e.g. with a photolabile protecting group can be affixed to the nanocrescent. Irradiation of the nanocrescent in the presence of the desired moiety bearing the corresponding avidin or streptavidin, or biotin, results in coupling of the moiety to the nanocrescent.

Where one or more moieties (e.g., the nanocrescent, the peptide (or other substrate, and/or the Raman label) bear reactive groups or are derivatized to bear reactive groups numerous coupling methods are readily available. Thus, for example, a free amino group is amenable to acylation reactions with a wide variety of carboxyl activated linker extensions that are well known to those skilled in the art. Linker extension can performed at this stage to generate terminal activated groups such as active esters, isocyanates, maleimides, and the like. For example, reaction of the peptide or amino-derivatized nanocrescent with one end of homobifunctional N-hydroxysuccinimide esters of bis-carboxylic acids such as terephthalic acid will generate stable N-hydroxysuccinimide ester terminated linker adducts that useful for conjugation to amines. Linker extension can also be accomplished with heterobifunctional reagents such as maleimido alkanoic acid N-hydroxysuccinimide esters to generate terminal maleimido groups for subsequent conjugation to thiol groups. An amino-terminated linker can be extended with a heterobifunctional thiolating reagent that reacts to form an amide bond at one end and a free or protected thiol at the other end. Some examples of thiolating reagents of this type which are well known in the art are 2-iminothiolane (2-IT), succinimidyl acetylthiopropionate (SATP) and succinimido 2-pyridyldithiopropionate (SPDP). The incipient thiol group is then available, after deprotection, to form thiol ethers with maleimido or bromoacetylated moieties or to interact directly with a gold surface. In various embodiments the amino group, e.g., of an amino-terminated linker can be converted a diazonium group and hence the substance into a diazonium salt, for example, by reaction with an alkali metal nitrite in the presence of acid, which is then reactive with a suitable nucleophilic moiety, such as, but not limited to, the tyrosine residues of peptides, and the like. Examples of suitable amino-terminated linkers for conversion to such diazonium salts include, but are not limited to aromatic amines (anilines), and may also include the aminocaproates and similar substances referred to above. Such anilines can readily be obtained by substituting into the coupling reaction between the an available hydroxyl group and an N-protected amino acid, as discussed above, the corresponding amino acid wherein the amino group is comprised of an aromatic amine, that is, an aniline, with the amine suitably protected, for example, as an N-acetyl or N-trifluoroacetyl group, which is then deprotected using methods well-known in the art. Other suitable amine precursors to diazonium salts will be suggested to one skilled in the art of organic synthesis.

Another favored type of heterobifunctional linker is a mixed active ester/acid chloride such as succinimido-oxycarbonyl-butyryl chloride. The more reactive acid chloride end of the linker preferentially acylates amino or hydroxyl groups, e.g., on the peptide to give N-hydroxysuccinimidyl ester linker adducts directly.

Yet another type of terminal activated group useful in the present invention is an aldehyde group. Aldehyde groups may be generated by coupling a free hydroxyl (e.g. on a peptide or derivatized nanocrescent) with an alkyl or aryl acid substituted at the omega position (the distal end) with a masked aldehyde group such as an acetal group, such as 1,3-dioxolan-2-yl or 1,3-dioxan-2-yl moieties, followed by unmasking of the group using methods well-known in the art. In various embodiments alkyl or aryl carboxylic acids substituted at the omega position with a protected hydroxy, such as, for example, an acetoxy moiety, may be used in coupling reactions, followed by deprotection of the hydroxy and mild oxidation with a reagent such as pyridinium dichromate in a suitable solvent, preferably methylene chloride, to give the corresponding aldehyde. Other methods of generating aldehyde-terminated substances will be apparent to those skilled in the art.

In certain embodiments, multiple peptides are conjugated to the surface of the nanocrescent, each being the same or different. In various embodiments approximately 5 to 500, more preferably about 10 to about 400, still more preferably about 20, 30, or 40 to about 200, 250, or 300, and most preferably about 50 to about 150 substrate molecules (e.g. peptides) are attached to the nanocrescent. In one embodiment, about 100 peptides are conjugated to the nanocrescent with direct reaction between Au and the thiol group on the peptide In various embodiments the substrate, e.g., a peptide that can be specifically cleaved by a proteolytically active protease is conjugated or tethered on the surface of the nanocrescent. In a preferred embodiment, the substrate peptide is an oligopeptide about 10~12 amino acid residues in length. However, In various embodiments the peptide can be as short as 4 amino acid residues, and as long as 100 amino acids. In various embodiments the peptides comprise substrates specifically recognized and cleaved by the corresponding proteases. The peptide can be synthesized and obtained commercially or the peptides can be made according to the methods described in Example 1. In certain embodiments at the amino terminus of the peptide, Raman active molecules such as biotin (FIG. 1A) or Rhodamine 6G (R19) (FIG. 1A) are preferably grafted through a short polyethyleneglycol or aminovaleric acid linker.

The foregoing coupling methods are meant to be illustrative and not limiting. Using the teaching provided herein numerous methods of coupling the substrate to the nanocrescent, and optionally the Raman label to the substrate, will be recognized by one of skill in the art.

Detection of the Raman Indicator.

A variety of detection units of potential use in Raman spectroscopy are known in the art and any known Raman detection unit may be used. A non-limiting example of a Raman detection unit is disclosed in U.S. Pat. No. 6,002,471. In this example, the excitation beam is generated by either a Nd:YAG laser at 532 nm (nanometer) wavelength or a Ti:sapphire laser at 365 nm wavelength. Pulsed laser beams or continuous laser beams may be used. The excitation beam passes through confocal optics and a microscope objective, and may be focused onto a substrate containing attached biomolecule targets. Raman emission light target(s) can be collected by the microscope objective and the confocal optics, coupled to a monochromator for spectral dissociation. The confocal optics can include a combination of dichroic filters, barrier filters, confocal pinholes, lenses, and mirrors for reducing the background signal. Standard full field optics can be used as well as confocal optics.

The Raman emission signal can be detected by a Raman detector. The detector can include an avalanche photodiode interfaced with a computer for counting and digitization of the signal. Where arrays of target(s) are to be analyzed, the optical detection system may be designed to detect and localize Raman signals to specific locations on a chip or grid. For example, emitted light may be channeled to a CCD (charge coupled device) camera or other detector that is capable of simultaneously measuring light emission from multiple pixels or groups of pixels within a detection field.

Other examples of Raman detection units are disclosed, for example, in U.S. Pat. No. 5,306,403, including a Spex Model 1403 double-grating spectrophotometer equipped with a gallium-arsenide photomultiplier tube (RCA Model C31034 or Burle Industries Model C3103402) operated in the single-photon counting mode. The excitation source is a 514.5 nm line argon-ion laser from SpectraPhysics, Model 166, and a 647.1 nm line of a krypton-ion laser (Innova 70, Coherent).

Various excitation sources include, but are not limited to, a nitrogen laser (Laser Science Inc.) at 337 nm and a helium-cadmium laser (Liconox) at 325 nm (U.S. Pat. No. 6,174, 677). The excitation beam can be spectrally purified with a bandpass filter (Corion) and may be focused on a substrate 140 using a 6.times. objective lens (Newport, Model L6X). The objective lens can be used to both excite the indicator(s) and to collect the Raman signal, by using a holographic beam splitter (Kaiser Optical Systems, Inc., Model HB 647-26N 18) to produce a right-angle geometry for the excitation beam and the emitted Raman signal. A holographic notch filter (Kaiser Optical Systems, Inc.) can be used to reduce Rayleigh scattered radiation. Alternative Raman detectors include, but are not limited to, an ISA HR-320 spectrograph equipped with a red-enhanced intensified charge-coupled device (RE-ICCD) detection system (Princeton Instruments). Other types of detectors may be used, such as charged injection devices, photodiode arrays or phototransistor arrays.

Figure 5:
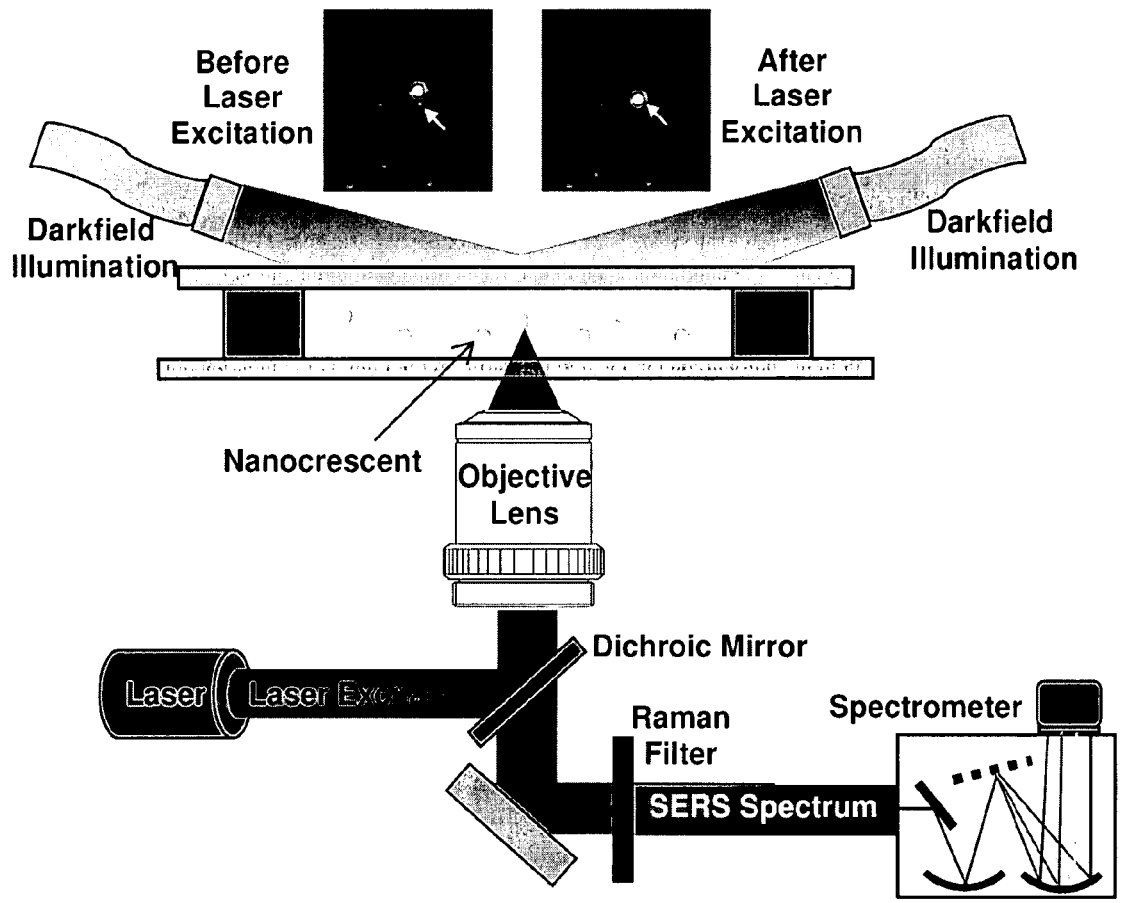
FIG. 5 illustrates a SERS microspectroscopy system and nanocrescent visualization. The peptide-conjugated nanocrescents are suspended in the reaction buffer in an enclosed transparent microchamber. The nanocrescents can be visualized using the dark field illumination from oblique angles as the bright dots shown in the inset pictures. The excitation laser is focused on the nanocrescents by a microscopy objective lens. The SERS signal is collected by the same objective lens and analyzed by a spectrometer.

One typical experimental system configuration shown in FIG. 5, comprising a microscopy system with Raman spectrometer was used to acquire Raman scattering spectra from single nanocrescents. In one embodiment, the system is comprised of inverted microscope such as the Carl Zeiss Axiovert 200 (Carl Zeiss, Germany), equipped with a digital camera and a monochromator with a spectrograph CCD camera, a laser source and an optical lens. In various embodiments the laser wavelength can be in the visible and near infrared region. In one preferred embodiment, a 785 nm semiconductor laser is used as the excitation source of Raman scattering, and the laser beam is focused by a 40× objective lens on the nanocrescent(s). The 785 nm or other near infrared light source can assure less absorption by biological tissue in the sample, and lower fluorescence background. For certain applications, however, lower wavelength excitation light might be more advantageous, and even UV light excitation can be used for applications. The excitation power can also be measured by a photometer to insure, in certain embodiments, an output of ~0.5 to 1.0 mW. The Raman scattering light can collected through the same optical pathway through a long-pass filter and analyzed by the spectrometer.

In various embodiments the protease presence, and/or concentration, and/or activity is determined in a biological sample. The biological sample can include essentially any biomaterial that it is desired to assay. Such biomaterials include, but are not limited to biofluids such as blood or blood fractions, lymph, cerebrospinal fluid, seminal fluid, urine, oral fluid and the like, tissue samples, cell samples, tissue or organ biopsies or aspirates, histological specimens, and the like.

In various embodiments peptide-conjugated nanocrescents are incubated with a sample suspected of containing protease molecules, preferably in a closed transparent microchamber. The microchamber is mounted on a thermal plate (e.g., at 37° C.) on an inverted Raman microscope with dark-field illumination for nanoparticle visualization. The nanocrescents are visualized using the darkfield illumination from oblique angles as the bright dots shown in the inset pictures. The excitation laser is focused on the nanocrescents by a microscopy objective lens. The SERS signal is collected by the same objective lens and analyzed by a spectrometer. The inset pictures show the ~0.8 mW excitation laser spot focusing on a single nanocrescent.

Real-time detection of digestion reactions can occur within 30 minutes. However, In certain embodiments the incubation can be as short as 1 to 5 minutes and as long as 24 hours, or longer, if the application needs longer incubation time. After initial centrifugal fractionation, the soluble content in crude cell lysate, urine sample, seminal fluid, cerebrospinal fluid, blood, or other sample materials can be directly incubated with the probes. The concentration of the probes is not critical because only one or few probes are examined every time. To specifically inhibit the protease-mediated proteolysis of the conjugated peptides, protease inhibitors can be introduced prior to the addition of the protease. For example, the peptide digestion by PSA is more than 90% suppressed after the addition of inhibitors given the same experimental conditions.

Figure 1B:
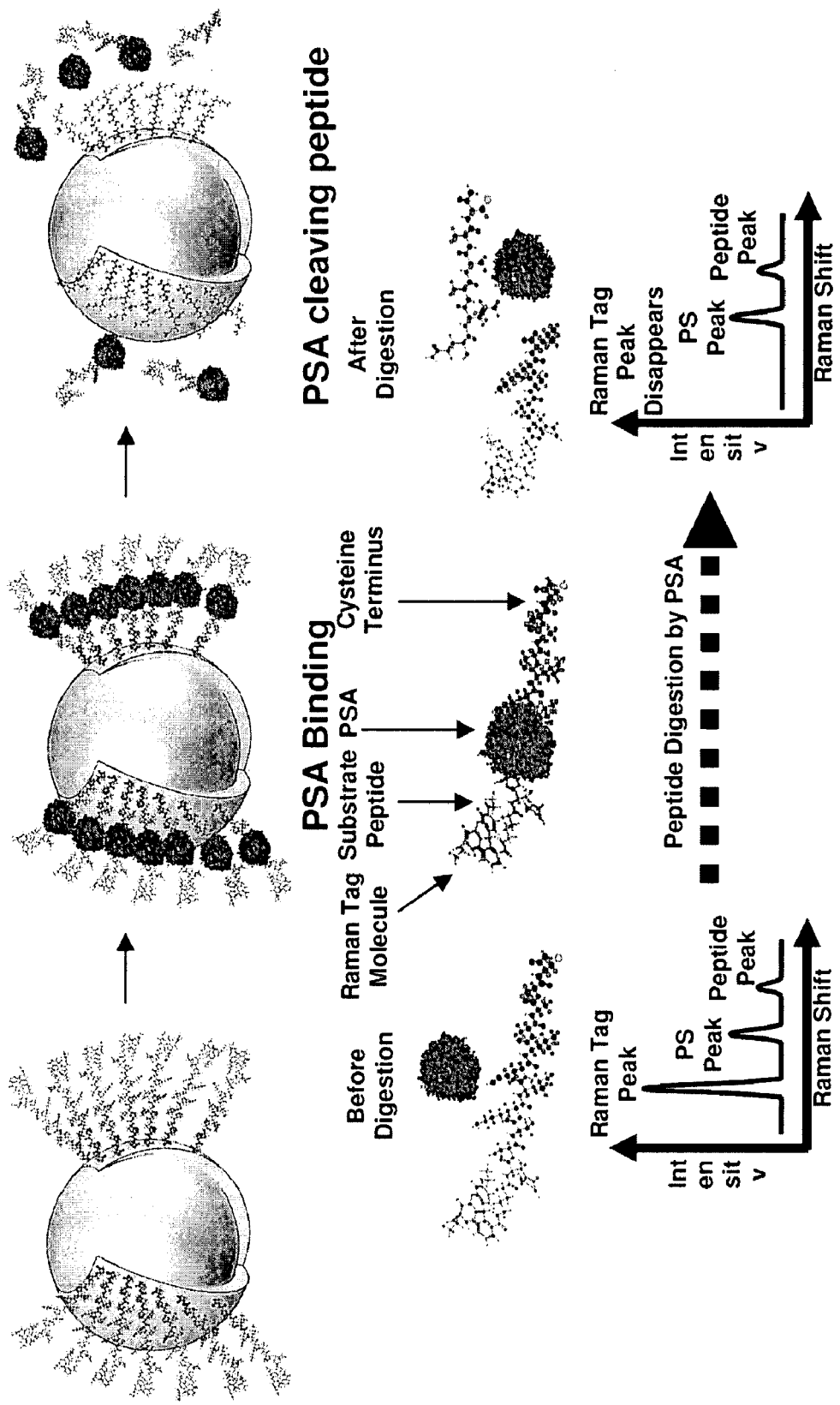

One detection scheme for protease presence, concentration and activity is shown in FIG. 1B. In this method, the peptide-conjugated SERS probe is provided to a solution or sample. Before the proteolytic reaction, the SERS spectrum of the peptide-conjugated nanocrescent contains the characteristic peaks from the Raman tag molecules, polystyrene nanoparticle, and the peptides. The digestion reaction by the protease should cleave the peptide at a predetermined cleavage site. For example, during the digestion reaction by PSA, the peptide HSSKLQ-L (SEQ ID NO:37) is cleaved between the Q and L residues, here denoted by a dashed line. The SERS spectra of the artificial peptides change after cleavage by the protease because the cleavage fragment containing the Raman tag molecules diffuse away from the nanocrescent surface, while the other fragments remain on the nanocrescent surface. The characteristic SERS peaks of the molecular moieties with the Raman active tag disappear due to the diffusive dislocation of the tag molecules from the nanocrescent surface into the solution after peptide digestion; therefore the existence and concentration of the proteolytically active PSA in solution can be probed by monitoring the SERS spectra of the peptide-conjugated nanocrescents. The Raman scattering signal of the attached peptide is then amplified by the nanocrescent and detected by a microscopy system as described comprising a Raman spectrometer to acquire Raman scattering spectra from single nanocrescents. The Raman spectrometer is preferably linked to a computer whereby the spectrometer can be controlled and the spectra can be obtained and a spectrograph can be observed.

Figure 6A:
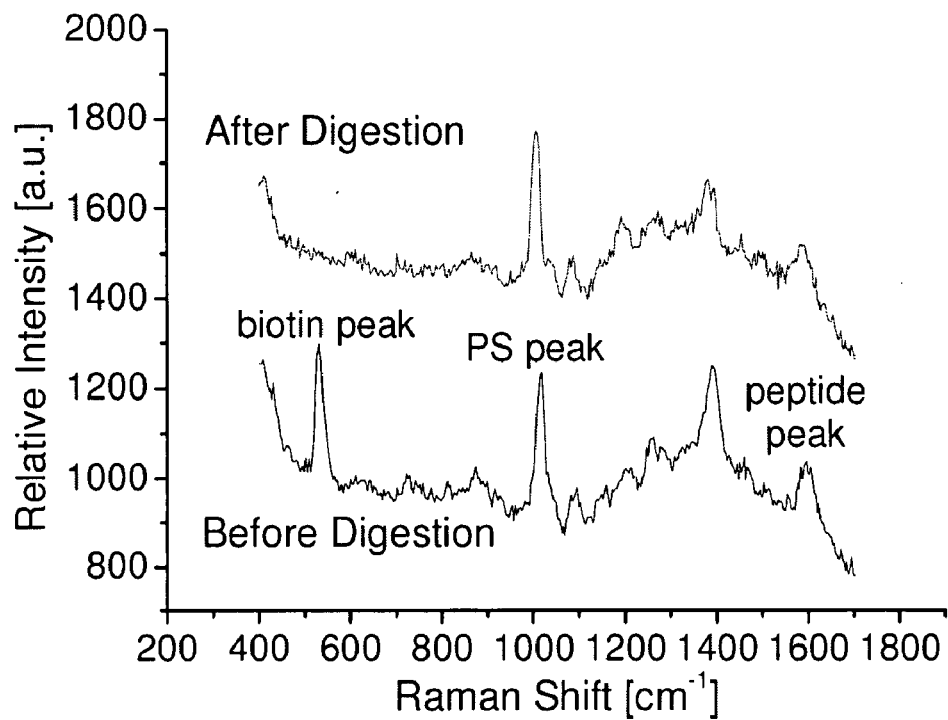
FIGS. 6A and 6B show typical SERS spectra of peptide-conjugated nanocrescents before and after PSA digestion reactions with biotin (FIG. 6A) and R19 (FIG. 6B) as the Raman tag molecules respectively.
Figure 6B:
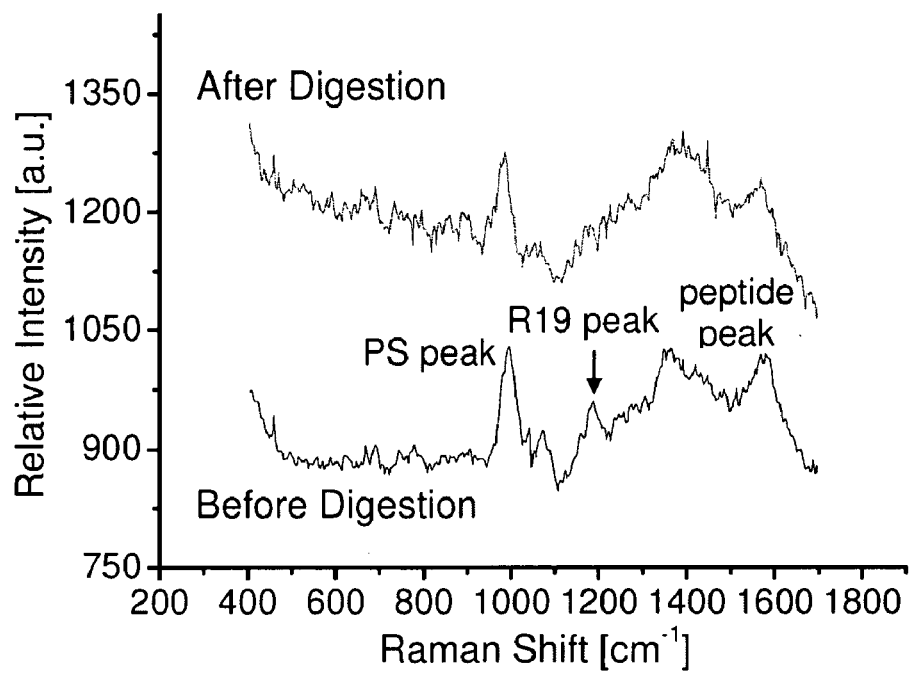

The digestion reaction dynamics can be monitored by time-resolved SERS spectra acquisitions. For example, peaks from the Raman tag molecules seen in the spectrograph, such as the peaks at 525 cm$^{-1}$ from biotin in FIG. 6A and 1183 cm$^{-1}$ from R19 in FIG. 6B, which almost completely disappear after the digestion reaction is finished (FIGS. 6A and B). As shown in the time-lapse SERS spectra in FIG. 6A, the digestion of the peptides on each nanocrescent, as monitored by the disappearance of the biotin peak at 525 cm$^{-1}$, takes ~30 min at a PSA concentration of 420 nM. For the peptide with R19 as the Raman tag molecule, the disappearance of the R19 peak at 1183 cm$^{-1}$ can be also observed after digestion by 420 nM PSA (FIG. 6B). Thus, the digestion of the peptide can be confirmed by the release of the Raman tag molecule and the disappearance of its Raman peaks. The temporal resolution of the real-time measurement can be around a few seconds and the reaction usually lasts for 10~20 minutes. The spectral detection can be done with ordinary spectral polychromer and cooled CCD camera. The monitored wavenumbers of Raman peaks range from 400 cm$^{-1}$ to 2000 cm$^{-1}$.

In certain embodiments, the time-lapse intensities of the Raman peak of the Raman active tag in the nanocrescent SERS probe in the digestion reaction is obtained with the protease, the protease with inhibitor, and a negative control, respectively. All the peak intensity values are normalized to the internal control peak (e.g., the peak intensity measured for the polystyrene core is 1003 cm$^{-1}$) and the initial peak intensity at the wavenumber of either the positive or negative control. The negative control can be a nanocrescent-peptide hybrid, in which the peptide is not a substrate of the protease(s) of interest and would not be cleaved by the protease(s) being studied. The results should indicate that the peptides are efficiently and specifically cleaved by PSA by the gradual disappearance of the peak intensity of the Raman active tag.

Figure 1C:
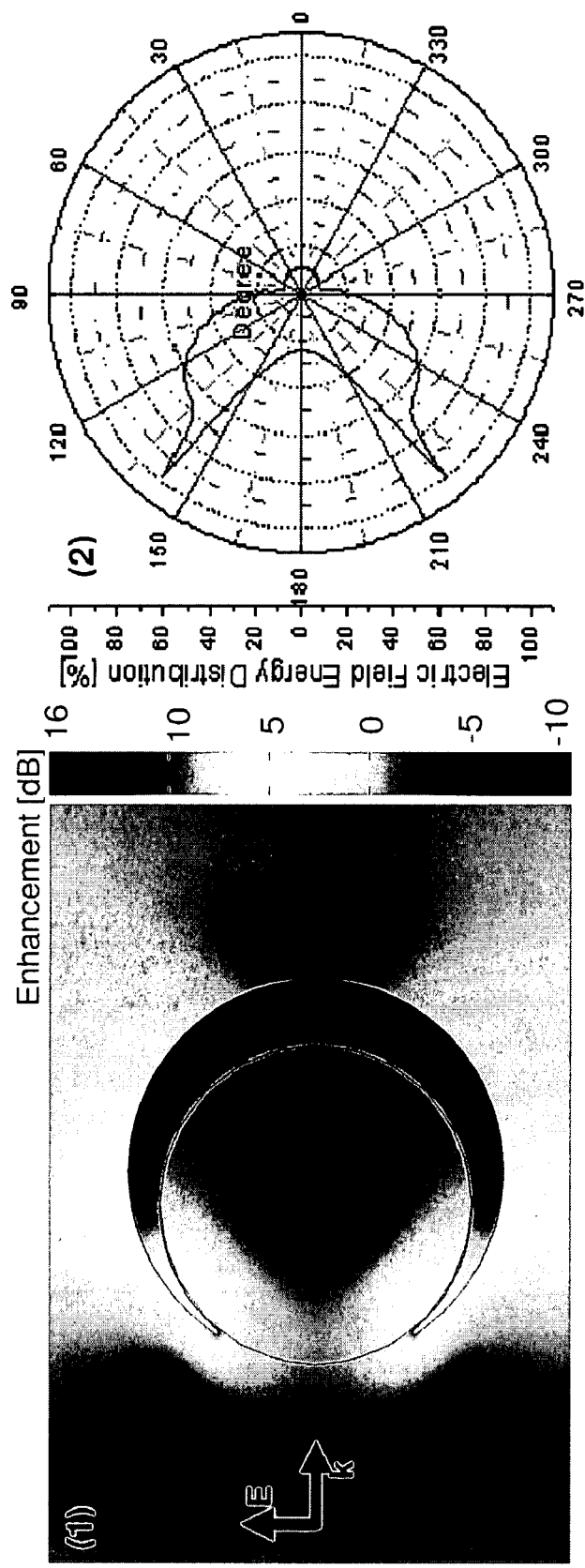

The nanocrescent particle serves as the Raman signal amplifier and the detected Raman signal comes from all the peptides tethered on the surface of nanocrescent particle. In certain embodiments at most 100 peptide molecules are attached per nanocrescent, it is likely that the nanocrescent surface with the highest SERS signal is not fully taken advantage of, and only a small percentage of the peptides are attached to the region that provides the greatest enhancement in electromagnetic field (FIG. 1C). The numerical simulation (FIG. 1C) indicates the amplitude of the local electric field can be enhanced by close to 20 dB (100 fold) especially around the sharp edge. Due to the fourth power relation between the electric field amplitude and the Raman enhancement factor, the peptide Raman signal could be amplified $10^8$ times by the nanocrescent.

Furthermore, because tens to hundreds of peptides are used in the conjugation reaction for each nanocrescent on average, the disappearance of the characteristic Raman peaks from the tag molecules is not abrupt. Since most of the enhanced field is concentrated around the tip area, which accounts for ~⅙ of total area of the nanocrescent, the actual molecule number contributing to the Raman scattering signal in this high enhancement area is less than 20, even if assuming the conjugation efficiency is 100%.

In certain embodiments the intensities of the Raman peak for the positive control as a function of PSA digestion time for various protease (e.g., PSA) concentrations are obtained before detection of protease (e.g., PSA) presence or activity in a sample. The typical SERS spectra of the peptide-conjugated nanocrescents with positive controls biotin and R19 Raman tag molecules for PSA conjugates are shown in FIGS. 6A and 6B, respectively. By comparing the SERS spectra before and 2 hours after the peptide digestion experiments, the Raman peaks from the nanocrescent core (e.g., polystyrene core, e.g. 1003 cm$^{-1}$) remain constant, and thus can also serve as an internal control. The digestion rate is related to the PSA concentration and PSA activity is typically observed in 30 min for a concentration 1 nM (with ~50% reduction in biotin signal intensity, data not shown). Some Raman peaks from the partial amino acid chain remaining on the nanocrescent surface after digestion may still appear in the spectra, although the peak positions have slight changes and the peak intensities decrease due to possible conformational changes upon peptide cleavage.

Figure 7A:
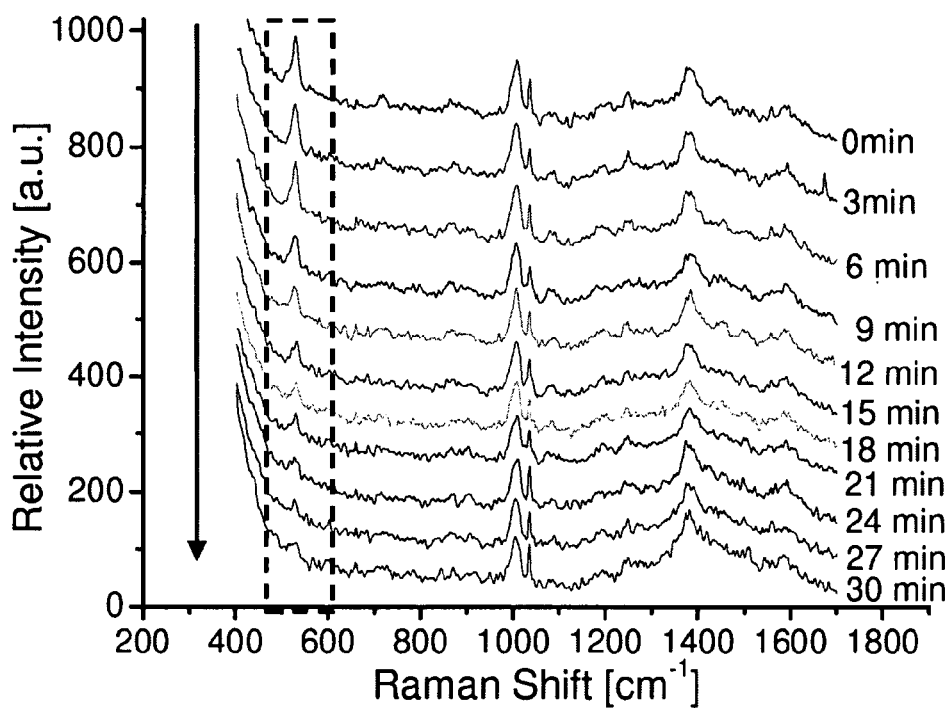
FIGS. 7A, 7B, 7C, and 7D show time-resolved SERS spectra in PSA digestion reactions.
Figure 7B:
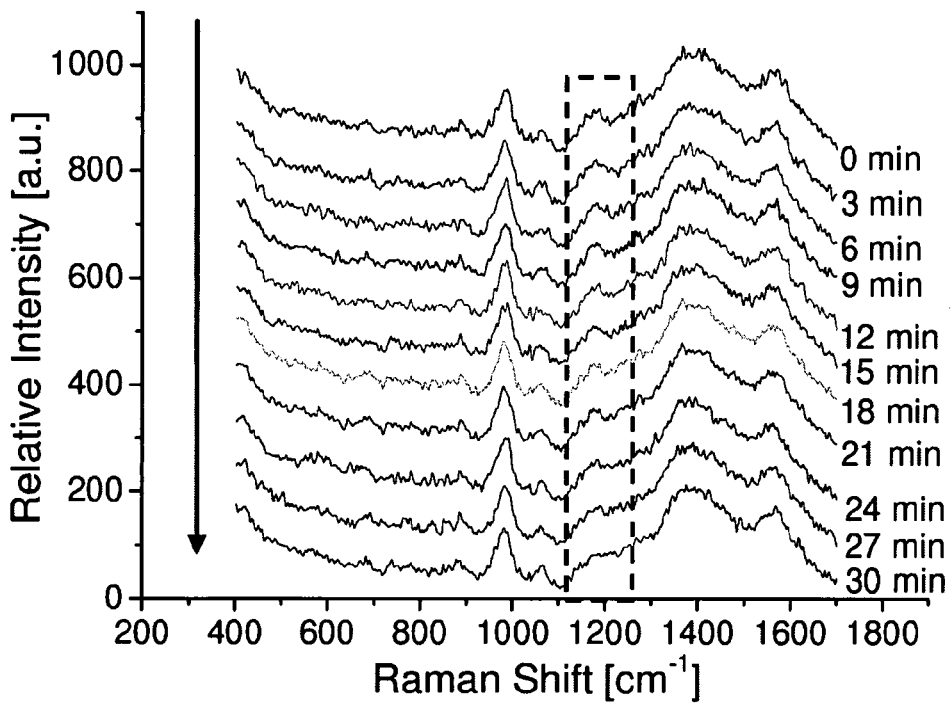
Figure 7C:
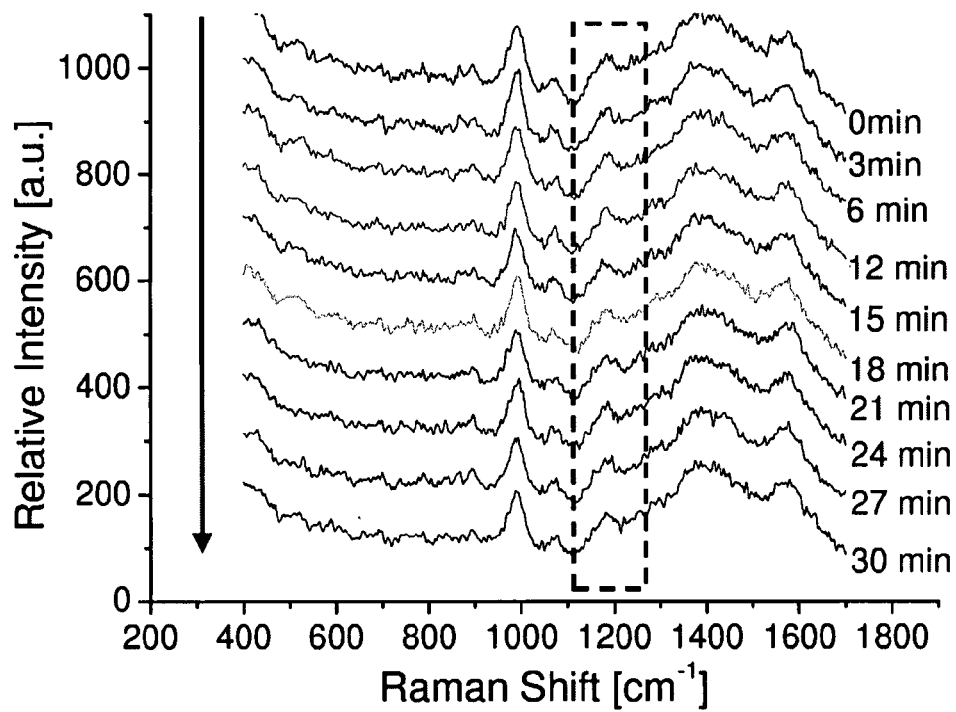
Figure 7D:
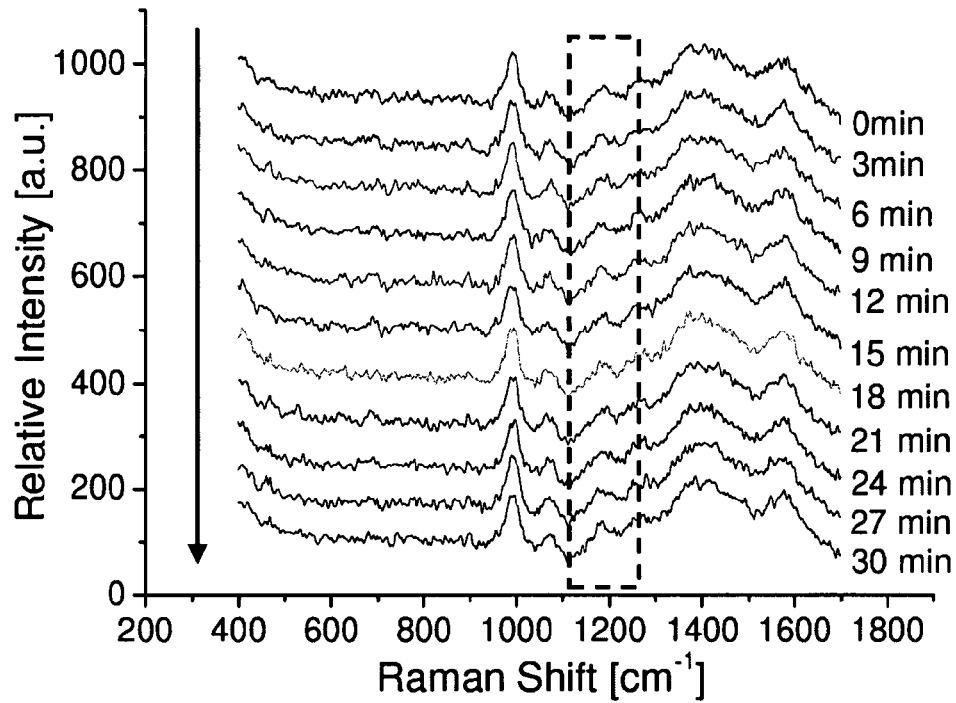

In certain embodiments, a negative control is run to show that the peptides are specifically cleaved by protease present in the sample. Example 1 shows the specificity of the conjugated peptides to PSA using other serine proteases such as Granzyme B, which can serve as a negative control. FIGS. 7C and 7D show the time-lapse SERS spectra of PSA-conjugated nanocrescents with R19 tag molecules in the two control experiments with the PSA inhibitor and the serine protease Granzyme B, which has orthogonal substrate specificity to PSA, respectively. In the control experiment of peptide digestion by 420 nM Granzyme B, the reaction rate showed no statistically significant difference from the inhibitor-treated reaction. The inability for Granzyme B to cleave the peptide is also expected as PSA has been shown to be the only protease for the HSSKLQ-LAAAC (SEQ ID NO:36) sequence in vivo.

In various embodiments the peptide-conjugated nanocrescent can be used as a specific screening tool to provide information on the concentration and proteolytic activity of the protease cancer biomarkers such as PSA, and others in biological samples obtained from patients in a clinical setting.

It is contemplated that one application of the indicators described herein is the incorporation of nanocrescents particle into microfluidic devices that can automate and facilitate sample delivery and washing process. The nanocrescent particles can be also delivered in real-time or immobilized in the device.

Other applications include the introduction of the nanocrescent particles into live cells or tissues, so that protease activity can be measured within the cells or tissues in real-time.

These examples are intended to be illustrative and not limiting. Using the teachings proved herein other uses and assays will be available to one of skill in the art.

Other Indicators.

While the foregoing discussion pertained to the use of nanocrescent-peptide conjugates (indicators) to detect active proteases, it will be appreciated that the same approach can be used to detect the presence of other hydrolytic biological molecules. Thus, for example the peptide protease substrate can be replaced with single or double-stranded nucleic acids (RNA or DNA), and the indicator can detect and/or quantify the presence of active nucleases. In such instances, the nucleic acid substrate will typically comprise one or more recognition sites for nucleases (e.g. restriction endonucleases). The nuclease recognition sites typically range in length from about 3 bp, 4 bp, 5 bp, 6 bp, 7 bp, 8 bp, 9 bp or 10 bp to about 15 bp, 20 bp, 25 bp, or 30 bp. In various embodiments the nucleic acid can range in length from about 3 bp to about 200 bp, preferably from about 4 bp to about 100 bp, more preferably from about 6, 8, 10, 16, or 20 bp to about 80, 60, 40, or 30 bp.

The indicators of the present invention are also not limited simply to the detection of hydrolytic/proteolytic activities. The indicators can also be used to detect and/or quantify binding interactions (e.g., protein/protein interactions, protein/DNA interactions, antibody/antigen interactions, receptor/ligand interactions, and the like).

Thus, for example, a protein, and/or sugar, and/or complex carbohydrate, and/or lipid, and/or nucleic acid "substrate" can be provided coupled to one or more nanocrescents. When the substrate is recognized and bound by a cognate binding partner the Raman spectrum will be changed and the interaction is detected.

Thus, for example a nucleic acid substrate can be provided attached to the nanocrescent(s) where the nucleic acid comprises one or more recognition sites for, e.g., a DNA binding protein. Binding of the nucleic acid by the DNA binding protein alters the Raman spectrum thereby producing a detectable signal. In certain embodiments the substrate further bears one or more Raman labels as described above. While the Raman label may not be cleaved in a simple binding interaction, the increased steric hindrance introduced by the bound moiety decreases association of the Raman label(s) with the nanocrescent(s) thereby substantially changing the Raman spectrum.

Other embodiments, utilize a "competitive" assay format for binding assays. In such assays, the analyte competes for the binding site(s) on the nanocrescent attached substrate(s) with a similar moiety bearing a Raman label. Displacement of the Raman-labeled moiety from its bound position on the substrate by the target analyte in the sample being assayed provides a detectable change in the Raman spectrum that is a measure of the amount of analyte present in the sample.

These assays are intended to be illustrative and not limiting. Using the teachings provided herein, other assay formats will be available to one of skill in the art.

Kits.

In another embodiment this invention provides kits for practice of the methods described herein. The kits typically comprise a container containing nanocrescents as described herein. The kits can additionally contain one or more substrates (e.g., protease substrates, nucleic acid substrates, etc.). The substrates can be provided in separate container(s) for subsequent conjugation to the nanocrescents or they can be provided as a nanocrescent conjugate. The kits can additionally comprise one or more Raman labels. The labels can be provided separately or as a component of the substrate-nanocrescent conjugate.

In various embodiments the kits, optionally, can include or more control reagents (e.g., a nanocrescent conjugated to a non-cleavable substrate) as described herein.

In various embodiments the kits, optionally include devices (e.g., syringe, swab, etc.) and or reagents (e.g., diluents and/or buffers) for the collection and/or processing of a biological sample.

In addition, the kits optionally include labeling and/or instructional materials providing directions (i.e., protocols) for the practice of the methods described herein. In certain embodiments the instructional materials describe the use of one or more indicators of this invention to detect and/or quantify the presence or activity of a protease. In various embodiments the instructional materials teach the use of the indicator and SERS detection scheme to detect nucleolytic and hydrolysis reactions. The presence, concentration and activity of various enzymes such as nuclease and hydrolase can be detected.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Peptide-Nanocrescent Hybrid SERS Probe for Optical Detection of Protease

Real-time in situ detection of protease enzymes is crucial for early-stage cancer screening and cell signaling pathway studies. Such detection, however, is difficult to realized using fluorescence or radioactive probes at small volumes (e.g., below 1 nL). In this example, we demonstrate the use of a hybrid optical probe that incorporates a nanocrescent particle peptides with artificial tag molecules. We performed a proof-of-concept study using PSA, one of the most prominent prostate cancer markers, and a serine protease present in patients' seminal fluid and serum. The Raman spectral signal from the tag molecules was enhanced by the nanocrescent and the signal was monitored as an indicator of peptide cleavage in a femtoliter reaction volume, at levels close to a single proteolytically active PSA molecule. The high reaction specificity of the peptide and the monitored Raman signal also minimized the false detection of other serine proteases and background Raman signal, which resulted in a high-fidelity and high-signal-to-noise-ratio cancer nanoprobe that can be easily incorporated into nano/microfluidic devices.

Here we introduce a new optical spectroscopic detection method for PSA proteolytic activity based on a PSA specific substrate peptide (Robert et al. (1997) *Biochemistry* 36: 3811-3819; Wu et al. (2004) *Clin. Chem.,* 50: 125-129; Brillard-Bourdet et al. (2002) *Eur. J Biochem.,* 269: 390-395; Rehault et al. (2002) *Biochim. Biophys. Acta* 1596: 55-62; Malm et al. (2000) *Prostate* 45: 132-139) conjugated crescent-shaped Raman nanoprobe, which can be used on minute sample volumes (femtoliters), integrated into microfluidics, or introduced intracellularly, and be used to optically monitor PSA proteolytic reactions in real time. The nanocrescent can serve as an individual surface enhanced Raman scattering (SERS) substrate (Lu et al. (2005) *Nano Lett.* 5: 119-124). Raman is a spectroscopic detection method for probing biochemical composition with abundant atomic level information without fluorophore labeling (Raman (1928) *Nature* 121: 619-619), however the Raman signal intensity (scattering cross-section) is much lower than fluorescence. Various SERS substrates have been developed to enhance the weak Raman scattering signals in chemical and biomolecule detections on the substrate surface over several orders of magnitude (Lu et al. (2005) *Nano Lett.* 5: 119-124; Lu et al. (2005) *Nano Lett.* 5: 119-124; Lu et al. (2005) *Nano Lett.* 5: 5-9; Haes et al. (2005)

J. Am. Chem. Soc. 127: 2264-2271; Jackson and Halas (2004) Proc. Natl. Acad. Sci., USA, 101: 17930-17935; Nie and Emory 91997) Science 275: 1102-1106; Liu and Lee (2005) Appl. Phys. Lett. 87: 074101).

The nanocrescents consist of a 100 nm polystyrene core and a 10~20 nm gold crescent shell. FIG. 1A shows the schematics and transmission electron micrograph of the nanocrescent. The nanocrescents are fabricated by angled Au deposition on the rotating polystyrene nanoparticle template (Lu et al. (2005) Nano Lett. 5: 119-124). The fabrication details were described previously (Id.). In this example, the polystyrene nanoparticle core is not removed and it serves as the internal control in the SERS detections. We then tether on the surface of the Au nanocrescent a substrate peptide that can be specifically cleaved by proteolytically active PSA. The peptides contain the sequence of HSSKLQ (SEQ ID NO:37) which has been shown to have very high specificity for proteolytically active PSA (Denmeade et al. (1997 Cancer Res 57, 4924-4930). It has been shown that HSSKLQ-L (SEQ ID NO:37) is cleaved by PSA but not by any other proteases in vivo in a mouse model (Denmeade et al. (2003) J. Natl. Cancer Inst. 95: 990-1000). A cysteine group at the carboxyl terminus of the peptide is used to attach the peptide to the Au surface, relying on the Au-thiol reaction to form a covalent bond. At the amino terminus of the peptide, Raman active molecules such as biotin (FIG. 1A) or rhodamine 6G (R19) (FIG. 1B) are grafted through a short polyethyleneglycol or aminovaleric acid linker. The detection scheme is shown in FIG. 1B. The SERS spectra of the artificial peptides change after cleavage by PSA, and the characteristic SERS peaks of the molecular moieties with the biotin or R19 tags disappear due to the diffusive dislocation of the tag molecules from the nanocrescent surface into the solution after peptide digestion; therefore the existence and concentration of the proteolytically active PSA in solution can be probed by monitoring the SERS spectra of the peptide-conjugated nanocrescents. The Raman scattering signal of the attached peptide is amplified by the nanocrescent. Our numerical simulation (FIG. 1C) indicates the amplitude of the local electric field can be enhanced by close to 20 dB (100 fold) especially around the sharp edge. Due to the fourth power relation between the electric field amplitude and the Raman enhancement factor, the peptide Raman signal could be amplified $10^8$ times by the nanocrescent.

FIG. 5 shows the experimental system configuration. The peptide-conjugated nanocrescents were incubated with PSA molecules in a closed transparent microchamber. The microchamber was mounted on a 37° C. thermal plate on an inverted Raman microscope with darkfield illumination for nanoparticle visualization. The inset pictures show the ~0.8 mW excitation laser spot focusing on a single nanocrescent.

The typical SERS spectra of the peptide-conjugated nanocrescents with biotin and R19 Raman tag molecules are shown in FIG. 6A and FIG. 6B, respectively. By comparing the SERS spectra before and 2 hours after the peptide digestion experiments, the Raman peaks from the polystyrene core, e.g. 1003 $cm^{-1}$, remains constant, which serves as an internal control. Some Raman peaks are from the partial amino acid chain remaining on the nanocrescent surface after digestion and they still appear in the spectra, although the peak positions have slight changes and the peak intensities decrease due to possible conformational changes upon peptide cleavage. Those peaks from the Raman tag molecules, such as 525 $cm^{-1}$ from biotin in FIG. 6A and 1183 $cm^{-1}$ from R19 in FIG. 6B, almost completely disappear after the digestion reaction is finished (FIGS. 6A and B).

The digestion reaction dynamics can be monitored by time-resolved SERS spectra acquisitions. Because ~100 peptides are used in conjugation reaction for each nanocrescent on average, the disappearance of the characteristic Raman peaks from the tag molecules is not abrupt. Since most of the enhanced field is concentrated around the tip area, which accounts for ~⅙ of total area of the nanocrescent, the actual molecule number contributing to the Raman scattering signal in this high enhancement area is less than 20, even if assuming the conjugation efficiency is 100% (FIG. 1C). As shown in the time-lapse SERS spectra in FIG. 6A, the digestion of the peptides on each nanocrescent, as monitored by the disappearance of the biotin peak at 525 $cm^{-1}$, takes ~30 mm at a PSA concentration of 420 nM. For the peptide with R19 as the Raman tag molecule, the disappearance of the R19 peak at 1183 $cm^{-1}$ can be also observed after digestion by 420 nM PSA (FIG. 6B).

In order to specifically inhibit the PSA-mediated proteolysis of the conjugated peptides, protease inhibitors were introduced prior to the addition of 420 nM PSA. We also tested the specificity of the conjugated peptides to PSA using other serine proteases such as Granzyme B, which serves as a negative control here. FIGS. 7C and 7D show the time-lapse SERS spectra of nanocrescents with R19 tag molecules in the above two control experiments with the PSA inhibitor and the serine protease Granzyme B, which has orthogonal substrate specificity to PSA, respectively. The peptide digestion by PSA is more than 90% suppressed after the addition of inhibitors given the same experimental conditions. In the control experiment of peptide digestion by 420 nM Granzyme B, the reaction rate showed no statistically significant difference from the inhibitor-treated reaction. The inability for Granzyme B to cleave the peptide is also expected as PSA has been shown to be the only protease for the HSSKLQ (SEQ ID NO:1) sequence in vivo (Denmeade et al. (2003) J. Natl. Cancer Inst. 95: 990-1000).

Figure 8A:
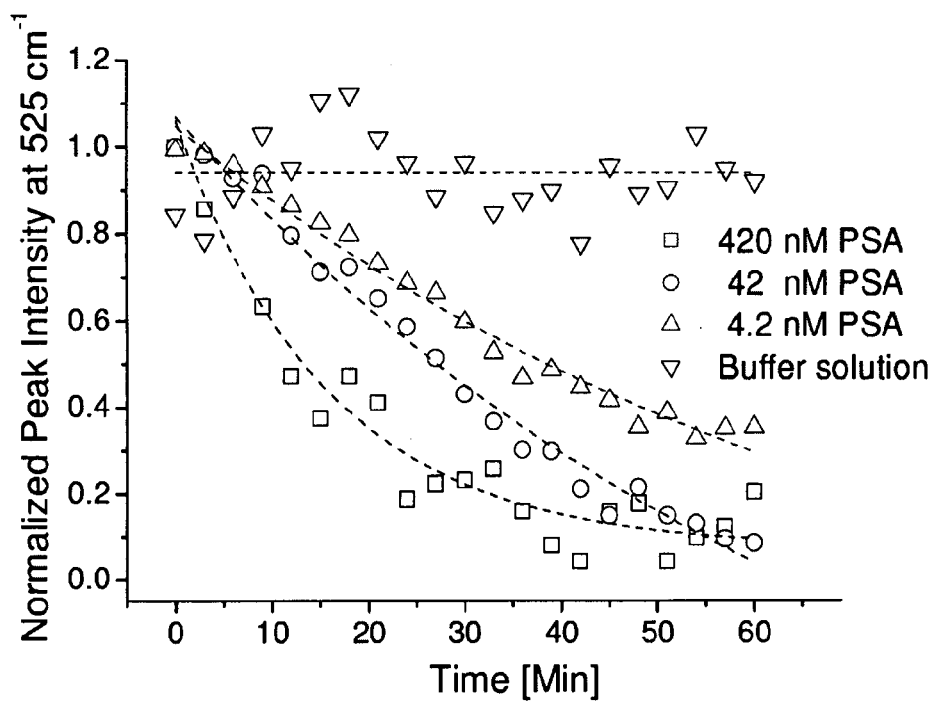
FIGS. 8A and 8B show time-dependent Raman peak intensities in PSA digestion reactions.
Figure 8B:
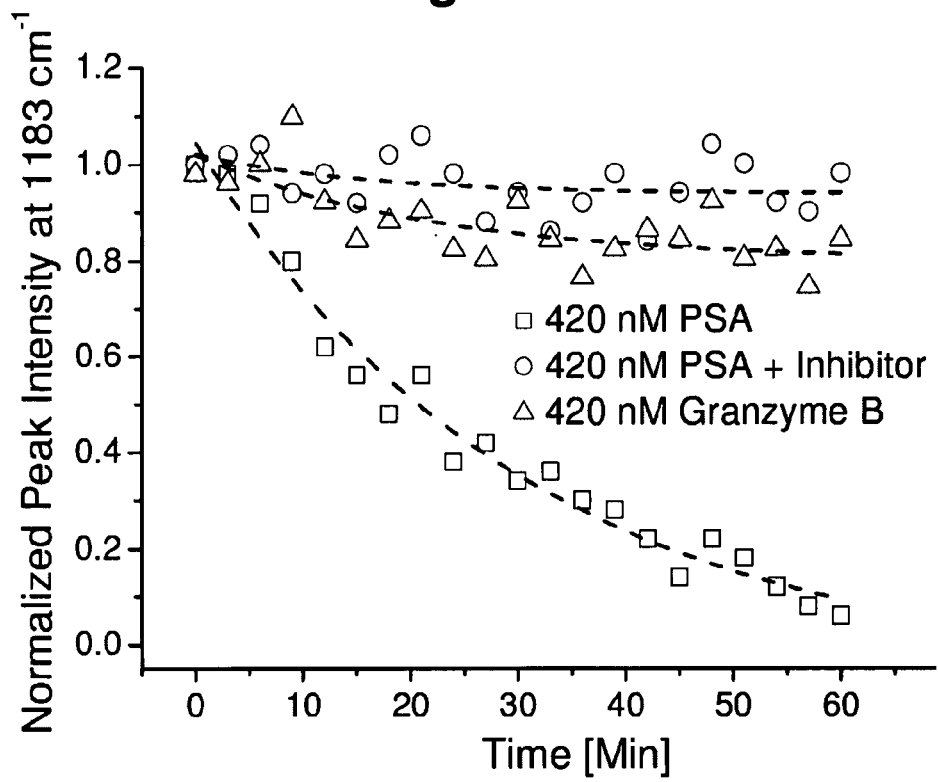

The digestion rate was related to the PSA concentration and we observed PSA activity in 30 min for a concentration 1 nM (with ~50% reduction in biotin signal intensity, data not shown). Since at most 100 peptide molecules are attached per nanocrescent, it is likely that the nanocrescent surface with the highest SERS signal is not fully taken advantage of, and only a small percentage of the peptides are attached to the region that provides the greatest enhancement in electromagnetic field (FIG. 1C). FIG. 8A shows the intensities of the biotin Raman peak at 525 $cm^{-1}$ as a function of PSA digestion time for the PSA concentration of 0 M (buffer solution), 4.2 nM, 42 nM and 420 nM. FIG. 8B shows the time-lapse intensities of the R19 Raman peak at 1183 $cm^{-1}$ in the digestion reaction with 420 nM PSA, 420 nM PSA with inhibitor, and 420 nM Granzyme B, respectively. All the peak intensity values are normalized to the internal control peak at 1003 $cm^{-1}$ and the initial peak intensity at 525 or 1183 $cm^-$. The results indicate that the peptides are efficiently and specifically cleaved by PSA, therefore this peptide-conjugated nanocrescent can be used as a specific screening tool to provide information on the concentration and proteolytic activity of the cancer biomarker PSA.

In conclusion, we have demonstrated the in vitro detection of proteolytically active PSA using a single peptide-conjugate nanocrescent SERS probe with at least nanomolar sensitivity. Since we use a highly focused laser beam as our excitation source, the detection volume is only about 10 femtoliter. The actual PSA molecule number for the nanomolar samples is close to the single molecule level. Compared to other cancer biomarker detection assays, our bioconjugated nanocrescent allows the detection of nanomolar concentrations of proteolytically active PSA molecules in femtoliter volumes, which is crucial especially for cancer screening at a single cancer cell level. The small volume requirement and sensitivity level makes it possible to detect PSA activity in captured circulating prostate cancer cells for indications of metastasis, which is not feasible with conventional techniques. In semen, the PSA concentration is 10-150 µM, with approximately two thirds of the PSA enzymatically active (Malm et al. (2000) *Prostate* 45: 132-139).

The sensitivity level achieved with the nanocrescent PSA probe (nanomolar range) is sufficient for a seminal fluid based assay, thus the nanocrescent SERS platform here could have potential clinical applications. In the current generation design, the PSA digestion site is between and the Glutamine (Q) and Leucine (L) residues, and is very close to the Au surface, thus the PSA peptide could be sterically hindered from the PSA enzyme and not optimally accessible. We envision that, with an additional spacer synthesized in between the substrate peptide sequence HSSKLQ (SEQ ID NO:1) and the Cys residue, we can improve the presentation of PSA substrate peptide HSSKLQ (SEQ ID NO:1) on the surface and thereby increase the detection sensitivity. The real-time reaction monitoring also provides critical information on PSA activity rather than just measuring the presence of the protein.

Two different Raman tag molecules are successfully utilized here indicating the potential of multiplexing the peptide-conjugated nanocrescents to detect two or more types of cancer-related proteases. The core can be made of magnetic material to allow spatial addressing of individual nanoparticles (Liu et al. (2005) *Adv. Mater.* 17: 2683-2688). The nanocrescent can also be manipulated by laser to address at high accuracy spatially (Liu et al. (2006) *Nat Mater* 5: 27-32), so that it could be multiplexed as high density arrays (with sub-microliter volume). Additional spatial multiplexing for multiple protease in a microarray or nanoarray format is possible. In addition, the magnetic or laser maneuverability allows biosensing at desired locations (Liu et al. (2005) *Adv. Mater.* 17: 2683-2688), which would be useful for obtaining in situ measurements intracellularly.

MATERIALS AND METHODS

PSA Preparation

PSA was purchased from CalBiochem (San Diego, Calif.). Cleavage of the substrate peptide immobilized on the Au nanocrescent was performed in buffer of 50 mM Tris-HCl, pH 8.0, 100 mM NaCl, and 0.1 mM EDTA, and the reaction was monitored in real-time in 37° C. PSA inhibitor was obtained from CalBiochem and added to the reaction solution following the manufacturer's instructions, so that the final reaction solution contained 5 µM AEBSF, 4.2 nM Aprotinin, 200 nM Elastatinal and 10 nM GGACK.

Peptide Synthesis

Biotin-Ttds-HSSKLQLAAAC-NH$_2$(1) (SEQ ID NO:36)

200 mg (0.140 mmol) of Rink Amide AM polystyrene resin (loading 0.69 mmol/g) was added to a 6 mL fritted syringe and swollen with DMF (4 mL). The fluorenylmethoxycarbonyl (Fmoc) protecting group was removed [treatment with 20% piperidine in DMF (2 mL) for 25 min], and the resin was filtered and washed with DMF (3×3 mL). To load the α-amino acid residues, the resin was subjected to repeated cycles of coupling conditions, followed by washing (3×3 mL) of DMF), Fmoc deprotection [treatment with 20% piperidine in DMF (2 mL) for 25 min], and washing again (3×3 mL of DMF). The conditions used for coupling the α-amino acids to the resin were subjection of the resin to a 0.4 M solution of the suitably protected acid [Fmoc-Cys(Trt, trityl)-OH (375 mg), Fmoc-Ala-OH (199 mg), Fmoc-Leu-OH (226 mg), Fmoc-Gln(Trt)-OH (391 mg), Fmoc-Lys(Boc, tert-butoxycarbonyl)-OH (300 mg), Fmoc-Ser(O-t-Bu)-OH (245 mg), or Fmoc-His(Trt)-OH (397 mg)] (0.640 mmol) which had been pre-activated by incubation with DIC (100 µL, 0.640 mmol) and HOBt (98 mg, 0.64 mmol) in DMF (1.5 mL) for 10 min. Each coupling was allowed to proceed for 4 h. After coupling and deprotection of the final α-amino acid residue, the Ttds linker was added by subjection of the resin to a 0.4 M solution of Fmoc-Ttds-OH (303 mg, 0.560 mmol) which had been pre-activated by incubation with DIC (88 µL, 0.56 mmol) and HOBt (86 mg, 0.56 mmol) in DMF (1.2 mL) for 10 min. The coupling was allowed to proceed overnight. The resin was washed with DMF (3×3 mL), the Fmoc protecting group was removed, and the resin was washed again with DMF (3×3 mL). The biotin group was incorporated by adding a slurry of biotin (137 mg, 0.560 mmol), PyBOP (281 mg, 0.540 mmol), and i-Pr$_2$NEt (94 µL, 0.54 mmol) in anhydrous DMF (1.5 mL) to the resin. After agitating the resin overnight, the resin was washed thoroughly with 20% piperidine in DMF (1×4 mL), DMF (3×4 mL), THF (3×4 mL), MeOH (3×4 mL), THF (3×4 mL), and CH$_2$Cl$_2$ (3×4 mL). The substrate was cleaved from the resin by incubation with a solution of 94:2:2:2 TFA/triisopropylsilane/H$_2$O/ethanedithiol (3 mL) for 1 h, purified using preparatory C 18 reverse-phase HPLC (CH$_3$CN/H$_2$O-0.1% TFA, 5-60% for 50 min, 8 mL/min, 210/220/254 nm detection for 100 min, t$_R$=31.8 min), and lyophilized. The purity was checked by HPLC-MS analysis (CH$_3$CN/H$_2$O-0.1% TFA, 5-95% for 14 min, 0.4 mL/min, 220 nm detection for 22 min, t$_R$=6.5 min). MS (ESI), m/z calcd for C$_{71}$H$_{121}$N$_{19}$O$_{22}$S$_2$: 1655.8. Found: m/z 828.2 (M+2H)$^{2+}$.

R19-Ava-HSSKLQLAAAC-NH$_2$ (2) (SEQ ID NO:36)

401 mg (0.277 mmol) of Rink Amide AM polystyrene resin (loading 0.69 mmol/g) was added to a 12 mL fritted syringe and swollen with N-methylpyrrolidinone (NMP) (4 mL). The Fmoc protecting group was removed by treatment with 1:2:2 piperidine/NMP/CH$_2$Cl$_2$ solution (3 mL) for 30 min, and the resin was filtered and washed with NMP (3×3 mL) and CH$_2$Cl$_2$ (3×3 mL). To load the α-amino acid residues, the resin was subjected to repeated cycles of coupling conditions (method A or method B), followed by washing (5×3 mL NMP, 5×3 mL CH$_2$Cl$_2$), Fmoc deprotection [treatment with 1:2:2 piperidine/NMP/CH$_2$Cl$_2$ solution (3 mL) for 30 min], and washing again with NMP (5×3 mL) and CH$_2$Cl$_2$ (5×3 mL). The first α-amino acid residue was loaded by addition of a preformed solution of Fmoc-Cys(Trt)-OH (1.17 g, 2.00 mmol), PyBOP (1.04 g, 2.00 mmol), and HOBt (270 mg, 2.00 mmol) in 1:1 NMP/CH$_2$Cl$_2$ (2 mL) onto the resin and the resulting slurry was stirred for 5 min on a wrist-action shaker, followed by addition of i-Pr$_2$EtN (0.55 mL, 4.0 mmol). The reaction was allowed to proceed for 5 h. The resin was then filtered, washed (5×3 mL NMP, 5×3 mL CH$_2$Cl$_2$), and dried under high vacuum. The loading of Cys was determined to be 0.60 mmol/g (78% yield). Successive couplings were achieved either by method A or method B. Method A consists of addition of a preformed solution of Fmoc-protected amino acid [Fmoc-Cys(Trt)-OH (1.17 g, 2.00 mmol), Fmoc-Ala-OH (622 mg, 2.00 mmol), Fmoc-Leu-OH (707 mg, 2.00 mmol), Fmoc-Gln(Trt)-OH (1.22 g, 2.00 mmol), Fmoc-Ser (tBu)-OH (767 mg, 2.00 mmol), and Fmoc-His(Trt)-OH (1.24 g, 2.00 mmol)], PyBOP (1.04 g, 2.00 mmol), and HOBt (270 mg, 2.00 mmol) in NMP/CH$_2$Cl$_2$ (1:1, 2 mL), followed by addition of i-Pr$_2$EtN (0.55 mL, 4.0 mmol). The reactions were allowed to proceed for at least 4 h. Method B consists of subjection of the resin to a 0.4 M solution of the suitably protected acid [Fmoc-Lys(Boc)-OH (375 mg)], which had been pre-activated by incubation with DIC (130 μL, 0.84 mmol) and HOBt (108 mg, 0.800 mmol) in DMF (2 mL) for 10 min. The coupling was allowed to proceed for 4 h. After each coupling the resin was filtered and washed (NMP: 5×3mL, CH$_2$Cl$_2$: 5×3 mL), followed by removal of the Fmoc protecting group. After coupling and deprotection of the final α-amino acid residue, the aminovaleric acid linker was added by subjection of the resin to a 0.4 M solution of Fmoc-S-Ava-OH (272 mg, 0.800 mmol) which had been pre-activated by incubation with DIC (120 μL, 0.80 mmol) and HOBt (108 mg, 0.800 mmol) in NMP (1 mL) for 10 min. The coupling was allowed to proceed overnight. The resin was filtered and washed (5×3mL NMP, 5×3 mL CH$_2$Cl$_2$), the Fmoc protecting group was removed, and the resin washed again. The rhodamine group was incorporated by adding a 0.4 M solution of rhodamine 19 (412 mg, 0.8 mmol), which had been pre-activated by incubation with DIC (130 μL, 0.84 mmol) and HOBt (108 mg, 0.800 mmol) in NMP (2 mL) for 10 min. The reaction was allowed to proceed for 6 h, the coupling procedure was repeated once more and the reaction was allowed to proceed overnight. The substrate was cleaved from the resin by incubation with a solution of 94:2:2:2 TFA/triisopropylsilane/H$_2$O/ethanedithiol (3 mL) for 2 h, purified using preparatory C18 reverse-phase HPLC (CH$_3$CN/H$_2$O-0.1% TFA, 5-95% for 50 min, 20 mL/min, 220/254/280 nm detection for 100 min, $t_R$=24.3 min), and lyophilized. MS (MALDI), m/z calcd for $C_{78}H_{116}N_{19}O_{17}S$: 1622.85. Found: m/z 1623.90.

SERS Spectroscopy

A microscopy system with Raman spectrometer was used to acquire Raman scattering spectra from single nanocrescents. The system consisted of a Carl Zeiss Axiovert 200 inverted microscope (Carl Zeiss, Germany) equipped with a digital camera and a 300 mm focal-length monochromator (Acton Research, MA) with a 1024×256-pixel cooled spectrograph CCD camera (Roper Scientific, NJ). A 785 nm semiconductor laser was used in our experiments as the excitation source of Raman scattering, and the laser beam was focused by a 40× objective lens on the nanocrescent. The excitation power was measured by a photometer (Newport, Calif.) to be ~0.8 mW. The Raman scattering light was then collected through the same optical pathway through a long-pass filter and analyzed by the spectrometer.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes, and to the same extent as if each was specifically and individually incorporated by reference.

What is claimed is:

1. An indicator for the detection of an active protease, said indicator comprising:
a nanocrescent attached to a peptide, wherein said nanocrescent comprises a core and a shell, and said peptide comprises a recognition site for said protease.

2. The indicator of claim 1, wherein said indicator further comprises a Raman label attached to said peptide.

3. The indicator of claim 2, wherein said Raman label is selected from the group consisting of a fluorophore, a chromophore, a quantum dot, a fluorescent microsphere, and biotin.

4. The indicator of claim 2, wherein said Raman label comprises a Rhodamine, a fluresceine, or an exogenous chemical molecule.

5. The indicator of claim 2, wherein said Raman label comprises a moiety selected from the group consisting of TRIT (tetramethyl rhodamine isothiol), NBC (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, 6-Carboxy-X-rhodamine, azomethines, cyanines, xanthines, succinylfluoresceins, aminoacridine, and cyanide (CN), thiol (SH), chlorine (Cl), bromine (Br), methyl, phorphorus (P), sulfur (S), SN, Al, Cd, Eu, and Te.

6. The indicator of claim 2, wherein said Raman label is directly attached to said peptide.

7. The indicator of claim 2, wherein said Raman label is attached to said peptide by a linker.

8. The indicator of claim 1, wherein said core comprises a material that provides a constant Raman spectrum.

9. The indicator of claim 8, wherein said core comprises a material selected from the group consisting of a plastic, a silica or other Group III, Group IV, or Group V material, a dextran, and a magnetic material.

10. The indicator of claim 9, wherein said core comprises a polystyrene.

11. The indicator of claim 1, wherein said nanocrescent comprises a metal selected from the group consisting of Ga, Au, Ag, Cu, Al, Ta, Ti, Ru, Ir, Pt, Pd, Os, Mn, Hf, Zr, V, Nb, La, Y, Gd, Sr, Ba, Cs, Cr, Co, Ni, Zn, Ga, In, Cd, Rh, Re, W, Mo, and oxides, alloys, mixtures, and/or nitrides thereof.

12. The indicator of claim 1, wherein said nanocrescent has an outer radius that ranges from about 20 to about 800 nm.

13. The indicator of claim 1, wherein said nanocrescent has an inner radius that ranges from about 10 nm to about 500 nm.

14. The indicator of claim 1, wherein said nanocrescent is characterized by an inner radius r, and outer radius R, and a center to center distance between the center of said the circle defined by said inner radius r and said outer radius R, wherein:
r ranges from about 10 nm to about 500 nm;
R ranges from about 20 nm to about 800 nm; and
d ranges from about 5 nm to about 300 nm.

15. The indicator of claim 1, wherein said nanocrescent is characterized by an inner radius r, and outer radius R, and a center to center distance between the center of said the circle defined by said inner radius r and said outer radius R, wherein:
r ranges from about 25 nm to about 500 nm;
R ranges from about 20 nm to about 800 nm; and
d ranges from about 5 nm to about 200 nm.

16. The indicator of claim 1, wherein said peptide comprises a recognition site for a protease selected from the group consisting of a serine protease, a metalloprotease, a cysteine protease, an aspartic acid protease, and a glutamic acid protease.

17. The indicator of claim 1, wherein said peptide comprises a recognition site for a protease in an apoptosis pathway.

18. The indicator of claim 17, wherein said peptide comprises a recognition site for a caspase.

19. The indicator of claim 17, wherein said peptide comprises a recognition site for a caspase selected from the group consisting of caspase-8, caspase-9, caspase-3, caspase-6, and caspase-7.

20. The indicator of claim 16, wherein said peptide comprises a recognition site for a thrombin.

21. The indicator of claim 16, wherein said peptide comprises a recognition site for a serine protease.

22. The indicator of claim 21, wherein said peptide comprises a PSA recognition site.

23. The indicator of claim 21, wherein said peptide comprises recognition site comprising the amino acid sequence HSSKLQ (SEQ ID NO:1).

24. The indicator of claim 1, wherein said peptide ranges in length from 2 amino acids to 30 amino acids.

25. The indicator of claim 24, wherein said peptide ranges in length from 2 amino acids to 10 amino acids.

26. The indicator of claim 1, wherein said peptide is attached directly to said nanocrescent.

27. The indicator of claim 1, wherein said peptide is attached to said nanocrescent by a linker.

28. The indicator of claim 1, wherein said peptide is attached to said nanocrescent by a thiol group.

29. The indicator of claim 2, wherein two different peptides are attached to said nanocrescent.

30. The indicator of claim 2, wherein more than two different peptides are attached to said nanocrescent.

31. The moiety of claim 1, wherein said indicator is a component of a Raman active substrate.

* * * * *

SEQUENCE LISTING

<160> NUMBER OF SEQ ID NOS: 39

<210> SEQ ID NO 1
<211> LENGTH: 6
<212> TYPE: PRT
<213> ORGANISM: Artificial
<220> FEATURE:
<223> OTHER INFORMATION: Synthetic protease substrate

<400> SEQUENCE: 1

His Ser Ser Lys Leu Gln
1               5

<210> SEQ ID NO 2
<211> LENGTH: 12
<212> TYPE: PRT
<213> ORGANISM: Artificial
<220> FEATURE:
<223> OTHER INFORMATION: Synthetic protease substrate

<400> SEQUENCE: 2

Ile Leu Glu Gly Leu Tyr Gly Leu Tyr Ala Arg Gly
1               5                   10

<210> SEQ ID NO 3
<211> LENGTH: 6
<212> TYPE: PRT
<213> ORGANISM: Artificial
<220> FEATURE:
<223> OTHER INFORMATION: Synthetic protease substrate
<220> FEATURE:
<221> NAME/KEY: misc_feature
<222> LOCATION: (2)..(3)
<223> OTHER INFORMATION: Xaa is any amino acid.
<220> FEATURE:

```
<221> NAME/KEY: misc_feature
<222> LOCATION: (6)..(6)
<223> OTHER INFORMATION: Xaa Ser or Gly.

<400> SEQUENCE: 3

Glu Xaa Xaa Tyr Gln Xaa
1               5

<210> SEQ ID NO 4
<211> LENGTH: 2
<212> TYPE: PRT
<213> ORGANISM: Artificial
<220> FEATURE:
<223> OTHER INFORMATION: Synthetic protease substrate

<400> SEQUENCE: 4

Arg Arg
1

<210> SEQ ID NO 5
<211> LENGTH: 2
<212> TYPE: PRT
<213> ORGANISM: Artificial
<220> FEATURE:
<223> OTHER INFORMATION: Synthetic protease substrate

<400> SEQUENCE: 5

Phe Arg
1

<210> SEQ ID NO 6
<211> LENGTH: 2
<212> TYPE: PRT
<213> ORGANISM: Artificial
<220> FEATURE:
<223> OTHER INFORMATION: Synthetic protease substrate

<400> SEQUENCE: 6

Phe Arg
1

<210> SEQ ID NO 7
<211> LENGTH: 2
<212> TYPE: PRT
<213> ORGANISM: Artificial
<220> FEATURE:
<223> OTHER INFORMATION: Synthetic protease substrate

<400> SEQUENCE: 7

Phe Pro
1

<210> SEQ ID NO 8
<211> LENGTH: 2
<212> TYPE: PRT
<213> ORGANISM: Artificial
<220> FEATURE:
<223> OTHER INFORMATION: Synthetic protease substrate

<400> SEQUENCE: 8

Phe Phe
1

<210> SEQ ID NO 9
<211> LENGTH: 2
<212> TYPE: PRT
<213> ORGANISM: Artificial
<220> FEATURE:
```

```
<223> OTHER INFORMATION: Synthetic protease substrate

<400> SEQUENCE: 9

Phe Lys
1

<210> SEQ ID NO 10
<211> LENGTH: 2
<212> TYPE: PRT
<213> ORGANISM: Artificial
<220> FEATURE:
<223> OTHER INFORMATION: Synthetic protease substrate

<400> SEQUENCE: 10

Leu Phe
1

<210> SEQ ID NO 11
<211> LENGTH: 2
<212> TYPE: PRT
<213> ORGANISM: Artificial
<220> FEATURE:
<223> OTHER INFORMATION: Synthetic protease substrate

<400> SEQUENCE: 11

Leu Tyr
1

<210> SEQ ID NO 12
<211> LENGTH: 2
<212> TYPE: PRT
<213> ORGANISM: Artificial
<220> FEATURE:
<223> OTHER INFORMATION: Synthetic protease substrate
<220> FEATURE:
<221> NAME/KEY: misc_feature
<222> LOCATION: (1)..(1)
<223> OTHER INFORMATION: Xaa is any amino acid.

<400> SEQUENCE: 12

Xaa Lys
1

<210> SEQ ID NO 13
<211> LENGTH: 2
<212> TYPE: PRT
<213> ORGANISM: Artificial
<220> FEATURE:
<223> OTHER INFORMATION: Synthetic protease substrate
<220> FEATURE:
<221> NAME/KEY: misc_feature
<222> LOCATION: (1)..(1)
<223> OTHER INFORMATION: Xaa is any amino acid.

<400> SEQUENCE: 13

Xaa Asp
1

<210> SEQ ID NO 14
<211> LENGTH: 2
<212> TYPE: PRT
<213> ORGANISM: Artificial
<220> FEATURE:
<223> OTHER INFORMATION: Synthetic protease substrate
<220> FEATURE:
<221> NAME/KEY: misc_feature
<222> LOCATION: (1)..(1)
<223> OTHER INFORMATION: Xaa is any amino acid.

<400> SEQUENCE: 14
```

Xaa Glu
1

<210> SEQ ID NO 15
<211> LENGTH: 2
<212> TYPE: PRT
<213> ORGANISM: Artificial
<220> FEATURE:
<223> OTHER INFORMATION: Synthetic protease substrate
<220> FEATURE:
<221> NAME/KEY: misc_feature
<222> LOCATION: (1)..(1)
<223> OTHER INFORMATION: Xaa is any amino acid.

<400> SEQUENCE: 15

Xaa Cys
1

<210> SEQ ID NO 16
<211> LENGTH: 4
<212> TYPE: PRT
<213> ORGANISM: Artificial
<220> FEATURE:
<223> OTHER INFORMATION: Synthetic protease substrate

<400> SEQUENCE: 16

Leu Phe Tyr Ala
1

<210> SEQ ID NO 17
<211> LENGTH: 6
<212> TYPE: PRT
<213> ORGANISM: Artificial
<220> FEATURE:
<223> OTHER INFORMATION: Synthetic protease substrate

<400> SEQUENCE: 17

Leu Trp Met Arg Phe Ala
1               5

<210> SEQ ID NO 18
<211> LENGTH: 7
<212> TYPE: PRT
<213> ORGANISM: Artificial
<220> FEATURE:
<223> OTHER INFORMATION: Synthetic protease substrate

<400> SEQUENCE: 18

Pro Gln Gly Ile Ala Gly Gln
1               5

<210> SEQ ID NO 19
<211> LENGTH: 9
<212> TYPE: PRT
<213> ORGANISM: Artificial
<220> FEATURE:
<223> OTHER INFORMATION: Synthetic protease substrate

<400> SEQUENCE: 19

Gly Leu Ser Ser Asn Pro Ile Gln Pro
1               5

<210> SEQ ID NO 20
<211> LENGTH: 4
<212> TYPE: PRT
<213> ORGANISM: Artificial
<220> FEATURE:
<223> OTHER INFORMATION: Synthetic protease substrate

```
<400> SEQUENCE: 20

Ile Glu Gly Arg
1

<210> SEQ ID NO 21
<211> LENGTH: 5
<212> TYPE: PRT
<213> ORGANISM: Artificial
<220> FEATURE:
<223> OTHER INFORMATION: Synthetic protease substrate
<220> FEATURE:
<221> NAME/KEY: misc_feature
<222> LOCATION: (5)..(5)
<223> OTHER INFORMATION: Xaa is any amino acid.

<400> SEQUENCE: 21

Tyr Glu Val Asp Xaa
1               5

<210> SEQ ID NO 22
<211> LENGTH: 5
<212> TYPE: PRT
<213> ORGANISM: Artificial
<220> FEATURE:
<223> OTHER INFORMATION: Synthetic protease substrate
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa is any amino acid.

<400> SEQUENCE: 22

Trp Glu His Asp Xaa
1               5

<210> SEQ ID NO 23
<211> LENGTH: 6
<212> TYPE: PRT
<213> ORGANISM: Artificial
<220> FEATURE:
<223> OTHER INFORMATION: Synthetic protease substrate
<220> FEATURE:
<221> NAME/KEY: misc_feature
<222> LOCATION: (5)..(5)
<223> OTHER INFORMATION: Xaa is any amino acid.
<220> FEATURE:
<221> NAME/KEY: misc_feature
<222> LOCATION: (6)..(6)
<223> OTHER INFORMATION: Xaa can be any naturally occurring amino acid

<400> SEQUENCE: 23

Val Asp Val Ala Asp Xaa
1               5

<210> SEQ ID NO 24
<211> LENGTH: 5
<212> TYPE: PRT
<213> ORGANISM: Artificial
<220> FEATURE:
<223> OTHER INFORMATION: Synthetic protease substrate
<220> FEATURE:
<221> NAME/KEY: misc_feature
<222> LOCATION: (5)..(5)
<223> OTHER INFORMATION: Xaa can be any naturally occurring amino acid

<400> SEQUENCE: 24

Asp Glu His Asp Xaa
```

```
<210> SEQ ID NO 25
<211> LENGTH: 5
<212> TYPE: PRT
<213> ORGANISM: Artificial
<220> FEATURE:
<223> OTHER INFORMATION: Synthetic protease substrate
<220> FEATURE:
<221> NAME/KEY: misc_feature
<222> LOCATION: (5)..(5)
<223> OTHER INFORMATION: Xaa can be any naturally occurring amino acid

<400> SEQUENCE: 25

Asp Met Gln Asp Xaa
1               5

<210> SEQ ID NO 26
<211> LENGTH: 5
<212> TYPE: PRT
<213> ORGANISM: Artificial
<220> FEATURE:
<223> OTHER INFORMATION: Synthetic protease substrate
<220> FEATURE:
<221> NAME/KEY: misc_feature
<222> LOCATION: (5)..(5)
<223> OTHER INFORMATION: Xaa can be any naturally occurring amino acid

<400> SEQUENCE: 26

Asp Glu Val Asp Xaa
1               5

<210> SEQ ID NO 27
<211> LENGTH: 5
<212> TYPE: PRT
<213> ORGANISM: Artificial
<220> FEATURE:
<223> OTHER INFORMATION: Synthetic protease substrate
<220> FEATURE:
<221> NAME/KEY: misc_feature
<222> LOCATION: (5)..(5)
<223> OTHER INFORMATION: Xaa is any amino acid.

<400> SEQUENCE: 27

Leu Glu Val Asp Xaa
1               5

<210> SEQ ID NO 28
<211> LENGTH: 5
<212> TYPE: PRT
<213> ORGANISM: Artificial
<220> FEATURE:
<223> OTHER INFORMATION: Synthetic protease substrate
<220> FEATURE:
<221> NAME/KEY: misc_feature
<222> LOCATION: (1)..(1)
<223> OTHER INFORMATION: Xaa is Trp or Leu.
<220> FEATURE:
<221> NAME/KEY: misc_feature
<222> LOCATION: (5)..(5)
<223> OTHER INFORMATION: Xaa is any amino acid.

<400> SEQUENCE: 28

Xaa Glu His Asp Xaa
1               5

<210> SEQ ID NO 29
<211> LENGTH: 5
<212> TYPE: PRT
<213> ORGANISM: Artificial
<220> FEATURE:
```

```
<223> OTHER INFORMATION: Synthetic protease substrate
<220> FEATURE:
<221> NAME/KEY: misc_feature
<222> LOCATION: (1)..(1)
<223> OTHER INFORMATION: Xaa is Trp or Leu
<220> FEATURE:
<221> NAME/KEY: misc_feature
<222> LOCATION: (5)..(5)
<223> OTHER INFORMATION: Xaa is any amino acid.

<400> SEQUENCE: 29

Xaa Glu His Asp Xaa
1               5

<210> SEQ ID NO 30
<211> LENGTH: 5
<212> TYPE: PRT
<213> ORGANISM: Artificial
<220> FEATURE:
<223> OTHER INFORMATION: Synthetic protease substrate

<400> SEQUENCE: 30

Val Glu Ile Asp Asn
1               5

<210> SEQ ID NO 31
<211> LENGTH: 5
<212> TYPE: PRT
<213> ORGANISM: Artificial
<220> FEATURE:
<223> OTHER INFORMATION: Synthetic protease substrate
<220> FEATURE:
<221> NAME/KEY: misc_feature
<222> LOCATION: (5)..(5)
<223> OTHER INFORMATION: Xaa can be any naturally occurring amino acid

<400> SEQUENCE: 31

Val Glu His Asp Xaa
1               5

<210> SEQ ID NO 32
<211> LENGTH: 5
<212> TYPE: PRT
<213> ORGANISM: Artificial
<220> FEATURE:
<223> OTHER INFORMATION: Synthetic protease substrate
<220> FEATURE:
<221> NAME/KEY: misc_feature
<222> LOCATION: (5)..(5)
<223> OTHER INFORMATION: Xaa can be any naturally occurring amino acid

<400> SEQUENCE: 32

Asp Glu Val Asp Xaa
1               5

<210> SEQ ID NO 33
<211> LENGTH: 5
<212> TYPE: PRT
<213> ORGANISM: Artificial
<220> FEATURE:
<223> OTHER INFORMATION: Synthetic protease substrate
<220> FEATURE:
<221> NAME/KEY: misc_feature
<222> LOCATION: (5)..(5)
<223> OTHER INFORMATION: Xaa can be any naturally occurring amino acid

<400> SEQUENCE: 33

Ile Glu Thr Asp Xaa
1               5
```

```
<210> SEQ ID NO 34
<211> LENGTH: 4
<212> TYPE: PRT
<213> ORGANISM: Artificial
<220> FEATURE:
<223> OTHER INFORMATION: Synthetic protease substrate
<220> FEATURE:
<221> NAME/KEY: misc_feature
<222> LOCATION: (4)..(4)
<223> OTHER INFORMATION: Xaa is any amino acid.

<400> SEQUENCE: 34

Leu Glu Asp Xaa
1

<210> SEQ ID NO 35
<211> LENGTH: 5
<212> TYPE: PRT
<213> ORGANISM: Artificial
<220> FEATURE:
<223> OTHER INFORMATION: Synthetic protease substrate
<220> FEATURE:
<221> NAME/KEY: misc_feature
<222> LOCATION: (5)..(5)
<223> OTHER INFORMATION: Xaa is any amino acid.

<400> SEQUENCE: 35

Leu Glu His Asp Xaa
1               5

<210> SEQ ID NO 36
<211> LENGTH: 5
<212> TYPE: PRT
<213> ORGANISM: Artificial
<220> FEATURE:
<223> OTHER INFORMATION: Synthetic protease substrate
<220> FEATURE:
<221> NAME/KEY: misc_feature
<222> LOCATION: (5)..(5)
<223> OTHER INFORMATION: Xaa is any amino acid.

<400> SEQUENCE: 36

Ile Glu Ala Asp Xaa
1               5

<210> SEQ ID NO 37
<211> LENGTH: 11
<212> TYPE: PRT
<213> ORGANISM: Artificial
<220> FEATURE:
<223> OTHER INFORMATION: Synthetic protease substrate

<400> SEQUENCE: 37

His Ser Ser Lys Leu Gln Leu Ala Ala Ala Cys
1               5                   10

<210> SEQ ID NO 38
<211> LENGTH: 7
<212> TYPE: PRT
<213> ORGANISM: Artificial
<220> FEATURE:
<223> OTHER INFORMATION: Synthetic protease substrate

<400> SEQUENCE: 38

His Ser Ser Lys Leu Gln Leu
1               5

<210> SEQ ID NO 39
<211> LENGTH: 5
<212> TYPE: PRT
```

```
<213> ORGANISM: Artificial
<220> FEATURE:
<223> OTHER INFORMATION: Synthetic protease substrate

<400> SEQUENCE: 39

Leu Ala Ala Ala Cys
1               5
```